(12) United States Patent
Saracen et al.

(10) Patent No.: US 7,552,490 B2
(45) Date of Patent: Jun. 30, 2009

(54) METHOD AND APPARATUS FOR PATIENT LOADING AND UNLOADING

(75) Inventors: Michael J. Saracen, Oakland, CA (US);
Aaron W. Carrano, San Jose, CA (US);
John W. Allison, Los Altos, CA (US);
Gopinath R. Kuduvalli, San Jose, CA (US)

(73) Assignee: Accuray Incorporated, Sunnyvale, CA (US)

( * ) Notice: Subject to any disclaimer, the term of this patent is extended or adjusted under 35 U.S.C. 154(b) by 367 days.

(21) Appl. No.: 11/339,717

(22) Filed: Jan. 24, 2006

(65) Prior Publication Data
US 2007/0169265 A1  Jul. 26, 2007

(51) Int. Cl.
*A61B 6/04* (2006.01)
*A61G 13/08* (2006.01)
(52) U.S. Cl. ............. 5/601; 5/600; 5/618; 378/209
(58) Field of Classification Search ............. 5/81.1 HS, 5/600–602, 607, 608, 610, 611, 617, 618, 5/622; 378/209
See application file for complete search history.

(56) References Cited

U.S. PATENT DOCUMENTS

| 455,168 | A | | 6/1891 | Case |
|---|---|---|---|---|
| 1,201,274 | A | | 10/1916 | Denquer |
| 2,893,164 | A | * | 7/1959 | Martin .................... 248/188.2 |
| 2,933,850 | A | * | 4/1960 | Martin .................... 248/188.2 |
| 3,753,592 | A | | 8/1973 | Jensen |
| 4,582,050 | A | * | 4/1986 | Willis ..................... 606/244 |
| 5,308,359 | A | * | 5/1994 | Lossing ................... 606/242 |
| 5,345,631 | A | * | 9/1994 | Saperstein et al. .......... 5/509.1 |
| 5,596,775 | A | | 1/1997 | Dimatteo |
| 5,724,970 | A | | 3/1998 | Votruba |
| 6,651,279 | B1 | | 11/2003 | Muthuvelan |
| 6,857,147 | B2 | | 2/2005 | Somasundaram |
| 6,948,688 | B1 | * | 9/2005 | Payne et al. ............. 248/188.2 |
| 2005/0028279 | A1 | | 2/2005 | De Mooy |
| 2005/0234327 | A1 | | 10/2005 | Saracen |
| 2007/0169265 | A1 | * | 7/2007 | Saracen et al. ............ 5/601 |
| 2009/0003532 | A1 | * | 1/2009 | Weber .................... 378/209 |

OTHER PUBLICATIONS

Coste-Manière, È., "Robotic whole body stereotacitc radiosurgery: clinical advantages of the CyberKnife® integrated system", The International Journal of Medical Robotics +Computer Assisted Sugery, 2005, www.roboticpublications.com, 14 pages.

(Continued)

*Primary Examiner*—Robert G Santos
(74) *Attorney, Agent, or Firm*—Blakely, Sokoloff, Taylor & Zafman LLP

(57) ABSTRACT

A method and apparatus of a positioning system are described to position an upper-half of a body relative to a head-end of a couch. The positioning system may be a patient positioning system and may include a treatment couch, a leg rest coupled to the treatment couch, and a drive mechanism coupled to the leg rest. The patient positioning system may also include a treatment couch, having a base portion of a treatment couch and plurality of detachable portions of the treatment couch. The plurality of detachable portions to adjust a height of the treatment couch to accommodate differing heights of patients.

33 Claims, 15 Drawing Sheets

OTHER PUBLICATIONS

"A Whole New Angle in Cardiology", Siemens Medical, 2003, Data, 8 pages.

"A Whole New Angle in Cardiology", Siemens Medical, 2003, Technical, 4 pages.

"Accuray Unveils the Next Generation in Robotic Radiosurgery", Accuray Incorporated Press Release, Oct. 17, 2005, 5 pgs., http://accuray.com/news/press101705.htm.

PCT International Search Report, PCT/US07/01918 filed Jan. 24, 2007 mailed Dec. 18, 2007.

PCT Written Opinion of the International Searching Authority, PCT/US07/01918 filed Jan. 24, 2007 mailed Dec. 18, 2007.

International Preliminary Report on Patentability, PCT/US2007/001918 filed Jan. 24, 2007, mailed Aug. 7, 2008.

* cited by examiner

METHOD AND APPARATUS FOR PATIENT LOADING AND UNLOADING

TECHNICAL FIELD

Embodiments of the present invention pertain to the field of patient positioning assembly for medical operations.

BACKGROUND

Treatment couches have been used in various medical operations. Some examples of treatment couches are surgery tables, operating tables, dentist chairs, and treatment couches for radiation treatment systems. Some examples of radiation treatment systems are gantry-based radiation treatment system and robot-based linear accelerator system. Treatment couches, in general, may be used to support a patient during these medical operations. Treatment couches may also be used to position a patient into a specific position in a treatment room. For example, a treatment couch may be used to position a patient with respect to a linear accelerator or other radiation sources for both gantry-based and robot-based treatment systems.

Another conventional design of a treatment couch used for medical operations is a reclining chair. It has two portions; a base portion, and a reclining portion. The reclining portion of the reclining chair allows a patient to sit back during a scanning procedure. In one conventional design, the reclining portion and the base portion move together to recline a patient backwards for treatment. In another conventional design, the reclining portion and the base portion may move in a folding and unfolding motion to and from one another. This folding and unfolding motion allows a patient to sit on the chair for patient loading purposes, and then allows the patient to sit back, or recline back for patient treatment purposes. These folding functions, however, do not include any mechanism to physically move the patient towards the head-end of the chair or table, or to physically move the patient to a specific position on the table or chair. These conventional designs merely position the patient forwards and backwards with respect to an upright sitting position of the reclining chair.

BRIEF DESCRIPTION OF THE DRAWINGS

The present invention is illustrated by way of example, and not by way of limitation, in the figures of the accompanying drawings.

DETAILED DESCRIPTION

The following description sets forth numerous specific details such as examples of specific systems, components, methods, and so forth, in order to provide a good understanding of several embodiments of the present invention. It will be apparent to one skilled in the art, however, that at least some embodiments of the present invention may be practiced without these specific details. In other instances, well-known components or methods are not described in detail or are presented in simple block diagram format in order to avoid unnecessarily obscuring the present invention. Thus, the specific details set forth are merely exemplary. Particular implementations may vary from these exemplary details and still be contemplated to be within the spirit and scope of the present invention.

Embodiments of a method and apparatus of a positioning system are described to position an upper-half of a body relative to a head-end of a couch. In one embodiment, the positioning system may be a patient positioning system. The patient positioning system may include a treatment couch, a leg rest coupled to the treatment couch, and a drive mechanism coupled to the leg rest. The drive mechanism moves the leg rest in one translational direction to adjust an upper-half of a body of a patient with respect to a head-end of the treatment couch. In another embodiment, the patient positioning system may include a treatment couch, having a base portion of a treatment couch and a plurality of detachable portions of the treatment couch. One detachable portion is coupled to the base portion of the treatment couch. The plurality of detachable portions are used to adjust a height of the treatment couch to accommodate differing heights of patients. In another embodiment, the patient positioning system may include a treatment couch, having a base portion of a treatment couch and a ratchet portion of the treatment couch coupled to the base portion of the treatment couch. The ratchet portion is used to adjust a height of the treatment couch to accommodate differing heights of patients.

It should be noted that the embodiments described herein have been described with reference to a body of a human patient for purposes of medical treatment. The term 'patient', as used herein, may refer to a human patient, or an animal patient. The embodiments described herein are not limited to adjusting or positioning a body of a patient for medical purposes, but may include adjusting or positioning a body (e.g., human or animal body) on a couch (e.g., chair, table, or other support members) for other non-medical purposes. Similarly, it should be noted that the embodiments described herein are not limited to a treatment couch used for purposes of medical treatment, but may also include a couch used for other (e.g., non-medical) purposes.

Figure 1:
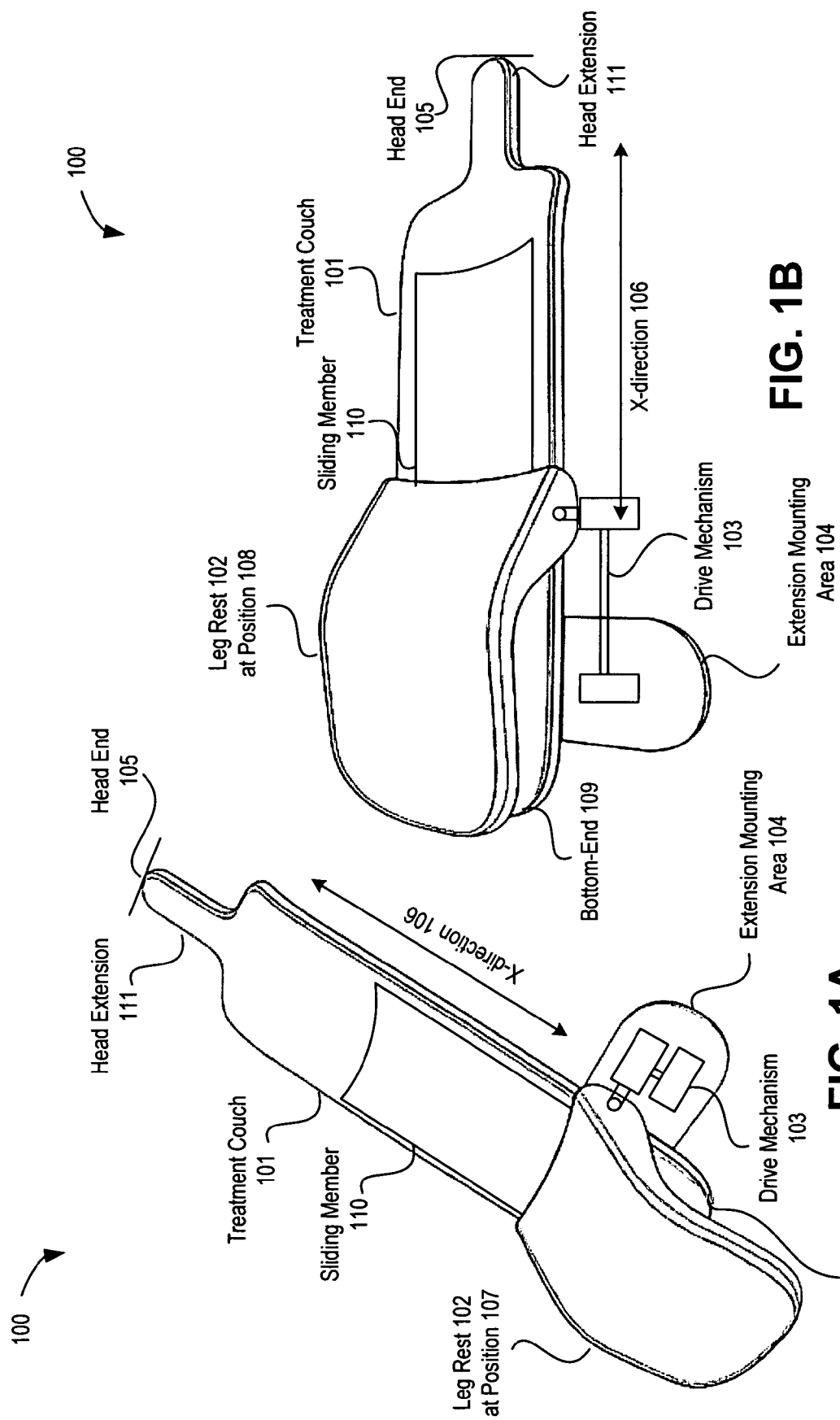
FIG. 1A illustrates one embodiment of a treatment couch having a leg rest and drive mechanism in a loading position.
FIG. 1B illustrates another embodiment of a treatment couch having a leg rest and drive mechanism in a treating position.

FIG. 1A illustrates one embodiment of a treatment couch having a leg rest and drive mechanism in a loading position. Patient positioning system 100 of FIG. 1A includes treatment couch 101, leg rest 102, drive mechanism 103, and extension mounting area 104. Treatment couch 101 is coupled to leg rest 102. Drive mechanism 103 is coupled to leg rest 102 and extension mounting area 104. Alternatively, drive mechanism 103 may be coupled to treatment couch 101 and leg rest 102. Extension mounting area 104 is coupled to treatment couch 101. Alternatively, extension mounting area 104 may be coupled to the leg rest 102.

The leg rest 102 of FIG. 1A is positioned at a first position on the treatment couch 101, position 107. When the leg rest 102 is positioned at position 107 it may be towards the bottom-end 109 of the treatment couch 101. Position 107 may be used for loading and/or unloading a patient onto and/or from treatment couch 101. It should be noted that patient, as used herein, may be a human patient, or alternatively, an animal patient. Drive mechanism 103 may be used to move the leg rest 102 in one translational direction, x-direction 106, relative to a head-end 105 of the treatment couch 101. In other words, the drive mechanism 103 may move the leg rest 102, which supports the lower-half of the patient's body, up and down with respect to the head-end 105. In effect, moving the leg rest 102 towards and/or from the head-end 105 of the treatment couch 101, the patient positioning system 100 adjusts an upper-half of the patient relative to the head-end 105 of the treatment couch 101.

In one embodiment, position 107 may be a loading position. Alternatively, position 107 may be a treating position for a patient whose height requires no adjustment of his/her upper-half of his/her body on the treatment couch 101. The loading position may be when the treatment couch 101 is tilted approximately 42 degrees from a perpendicular axis to the floor of the treatment room. In another embodiment, the loading position may be at approximately 50 degrees. By lowering the loading position from 42 degrees to 50 degrees, the distance that the leg rest must travel from the loading position to the treating position may be lowered from approximately 28 inches to 24 inches. These exemplary embodiments of 42 degrees and 50 degrees are for loading a patient in a non-horizontal position; however, it should also be noted that the loading position may be in a horizontal position, 90 degrees from the perpendicular axis to the floor of the treatment room. Alternatively, other degrees of tilt for the loading position may be used based on patient comfort.

FIG. 1B illustrates another embodiment of a treatment couch having a leg rest and drive mechanism in a treating position. Patient positioning system 100 of FIG. 1B includes treatment couch 101, leg rest 102, drive mechanism 103, and extension mounting area 104. Treatment couch 101 is coupled to leg rest 102. Drive mechanism 103 is coupled to leg rest 102 and extension mounting area 104. Alternatively, drive mechanism 103 may be coupled to treatment couch 101 and leg rest 102. Extension mounting area 104 is coupled to treatment couch 101. Alternatively, extension mounting area 104 may be coupled to the leg rest 102.

Leg rest 102 of FIG. 1B is positioned at a second position on the treatment couch 101, position 108. When the leg rest 102 is positioned at position 108 it may be towards the head-end 105 of the treatment couch 101. Position 108 may be used for treating a patient on treatment couch 101. Alternatively, position 108 may be used as a horizontal loading position.

In one embodiment, the treating position 108 may be where the head of the patient is positioned or aligned so that there is substantially no space between the head of the patient and the head-end 105 of the treatment couch 101. In one embodiment, the treating position 108 may be where the head of the patient is located within the head extension 111. Head extension 111 may be less in width than the treatment couch 101 to allow a radiation source to be positioned closer to the patient's head. It should be noted, however, that the treatment couch 101 may not include a head extension 111 and the patient's head may be positioned to have a certain distance (e.g., 908) between the head of the patient and the head-end 105, for example, within six inches. This may allow a radiation source to be positioned with respect to the head of the patient with minimal interference from the treatment couch 101, or without any interference from the treatment couch 101. For example, if a shorter patient (e.g., one percentile female height of 58.1 inches). In one embodiment, after a patient is loaded onto the treatment couch 101 in position 107, the leg rest 102 may be moved in the translational x-direction 106 up or down (away from and towards the head-end 106) to position the patient on the treatment couch to a treating position, position 108. However, position 108 may be used as a loading position. The patient may be loaded onto the treatment couch in position 108, and then, the leg rest 102 may be moved in the translational x-direction 106 up or down (away from or towards the head-end 106) to position the patient on the treatment couch to a treating position, position 107. The loading position may be a seated position where the treatment couch is tilted at an angle, or alternatively, a horizontal position where the treatment couch is parallel to the ground of the treatment room.

It should be noted that the term treating position, as used herein, is used to describe how the patient is positioned or adjusted on the treatment couch 101 relative to the head-end 106 of the treatment couch 101. The term treatment position, as used herein, is used to describe how the treatment couch 101 is positioned in a treatment room and/or relative to a radiation source. It should also be noted that the treatment positions within a treatment room may be a seated position where the treatment couch is tilted at an angle from the ground of the treatment room (as illustrated in FIG. 1A), or alternatively, a horizontal position where the treatment couch is substantially parallel to the ground of the treatment room (as illustrated in FIG. 1B). In other words, the patient may be positioned (or adjusted) on the treatment couch 101 relative to a head-end 106, and positioned in the treatment room (by positioning the treatment couch 101). These positioning operations may be done concurrently or subsequently to one another.

As previously described, drive mechanism 103 may be used to move the leg rest 102 in one translational direction, x-direction 106, relative to a head-end 105 of the treatment couch 101. In other words, the drive mechanism 103 may move the leg rest 102, which supports the lower-half of the patient's body, up and down with respect to the head-end 105. In effect, by moving the leg rest 102 towards and/or from the head-end 105 of the treatment couch 101, the patient positioning system 100 adjusts an upper-half of the patient relative to the head-end 105 of the treatment couch 101. In one embodiment, position 108 may be a treating position.

In one embodiment, the treating position 108 may be where the head of the patient is positioned or aligned so that there is substantially no distance between the head of the patient and the head-end 105 of the treatment couch 101. In one exemplary embodiment, the distance between the head of the patient and the head-end 105 for the treating position 108 may have a range of approximately zero to six inches. This may allow a radiation source to be positioned with respect to the head of the patient with minimal interference from the treatment couch 101, or without any interference from the treatment couch 101. For example, if a shorter patient (e.g., 1 percentile female height of 58.1 inches) is loaded onto the treatment couch 101 in position 107, the patient's head will not be aligned or positioned at the top (e.g., head-end 105) of the treatment couch 101 because of the height of the shorter patient. However, by moving the leg rest 102 of the treatment couch 101 towards the head-end 105 of the treatment couch 101 (e.g., from position 107 to position 108), the patient's head may become aligned or positioned at the top (e.g., head-end 105) of the treatment couch 101.

In one embodiment, a sliding member 110 may be coupled to the leg rest 102. The slide member 110 may be attached to the leg rest so that it the slide member 110 moves with the translational motion of the leg rest 102 in the x-direction 106. Slide member 110 may be a thin back piece. The slide member 110 may be used to reduce the friction between the upper-half of the patient's body and the treatment couch 101. The slide member 110 may also be used to prevent the upper-half of the patient's back from directly lying on the treatment couch 101 to help prevent the patient from getting pinched between the leg rest 102 and the treatment couch 101 as the leg rest 102 moves from one position to another in the x-direction 106.

In one exemplary embodiment, a mask may be placed on the patient's head to secure the patient to the treatment couch 101 and prevent the head from moving during treatment. The mask may be coupled to a mounting device, which secures the mask to the treatment couch 101. In order to secure the mask to the patient's head, the patient's head must be aligned and positioned correctly towards the head-end 105 of the treatment couch. By moving the leg rest 102 using the drive mechanism 103, the upper-half of the patient may be adjusted relative to the head-end 105 of the treatment couch 101, and may be positioned to allow the mask to be secured or mounted to the treatment couch 101.

Extension mounting area 104 of FIGS. 1A and 1B may be used to mount the treatment couch 101 to a stand, to a robotic arm, or to a motorized mechanism. It should be noted that the extension mounting area may also be disposed at another location along the periphery of the treatment couch 101 other than as shown in FIGS. 1A and 1B, such as at the bottom-end 109 of treatment couch 101. In one embodiment, the treatment couch 101 is coupled to a robotic arm.

In one exemplary embodiment, the robotic arm may be used to position the treatment couch in five degrees of freedom. The five degrees of freedom may include two rotational axes for translational movements along mutually orthogonal x-, and y-horizontal coordinate axes; and three rotational axes for roll-, pitch-, and yaw-rotational movements about x-, y-, and z-axes, respectively. In another embodiment, the robotic arm may position the treatment couch using six degrees of freedom, for example, five rotational degrees of freedom as previously described, and one substantially vertical, linear degree of freedom. The one substantially vertical, linear degree of freedom may include a substantial linear axis for translation along a substantially vertical line in a z-coordinate axis perpendicular to the horizontal, x-, and y-coordinate axes. In another embodiment, the robotic arm may position the treatment couch using seven degrees of freedom, six rotational degrees of freedom, and one substantially vertical, linear degree of freedom. Alternatively, the robotic arm may include less than five degrees of freedom, such as two or three degrees of freedom.

The robotic arm may be coupled directly to the treatment couch 101 in a mounting region, or alternatively to the extension mounting area 104. Alternatively, if the patient treatment couch 101 is sufficient thickness in the mounting region, the robotic arm may be mounted directly to an edge side of the treatment couch without the use of extension mounting area. The mounting of robotic arm on extension mounting area 104 (or, alternatively, on to edge side) may be used to allow the robotic arm to be out of the imaging field of view for all supported treatment positions. It should also be noted that drive mechanism 103 may be mounted to a mounting region of the treatment couch 101, or alternatively, to the extension mounting area 104.

Figure 2:
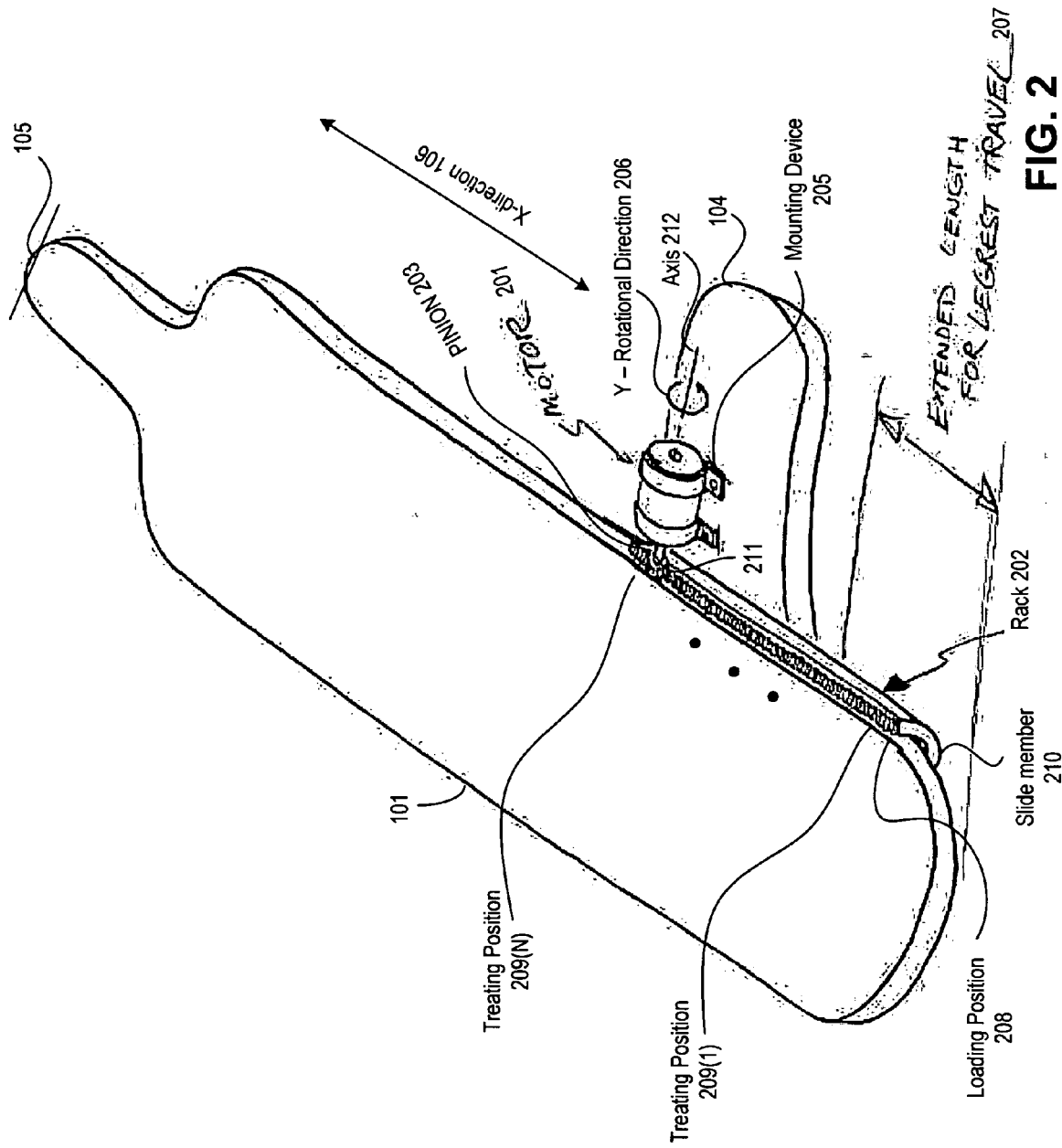
FIG. 2 illustrates one embodiment of a motorized drive mechanism including a rack and pinion gear.

FIG. 2 illustrates one embodiment of a motorized drive mechanism including a rack and pinion gear. The rack and pinion gear includes a motor 201, rack 202, and pinion 203. The rack and pinion gear is used to convert rotational motion of the motor 201 in the y-rotational direction 206 about axis 212 into linear motion of the leg rest 102 or treatment couch 101 in the x-direction 106. Motor 201 is mounted to extension mounting area 104 via mounting device 205. The motor 201 rotates pinion 203. Alternatively, the pinion 203 may be attached to a shaft (e.g., drive shaft 211), which is attached to the motor 201. The pinion 203 is operatively coupled to the rack 202. The rack 202 may include multiple teeth in which the pinion 202 may engage. As the motor 201 rotates the pinion 203 (or drive shaft 211 coupled to the pinion 203) in the y-rotational direction 206 about axis 212, the pinion 203 engages the teeth of the rack 202, causing the rack 202 to move linearly in the x-direction 106. In one embodiment, the rack is coupled to the leg rest 102 (e.g., via slide member 210). In another embodiment, the rack is coupled to the treatment couch 101, and the treatment couch moves relative to a leg rest 102.

In one embodiment, as illustrate in FIG. 2, the motor 201 is mounted to the extension mounting area 104 of the treatment couch 101, and the rack 202 is mounted to slide member 210. The slide member 210 may move along a rail slide mounted to the treatment couch 101. The rail slide may be used to facilitate translational motion of the leg rest 102 relative to a head-end 105 of the treatment couch 101. The rail slide may be mounted to the external surface of the treatment couch 101, or alternatively, it may be embedded within the treatment couch 101.

In another embodiment, rack 202 may be coupled directly to the treatment table 101, in which case, the pinion 203 drives the rack 202 to move the treatment couch 101 relative to the leg rest 102 in the x-direction 106. Alternatively, slide member 210 may be coupled to the leg rest 102, in which case, the pinion 203 drives the rack 202 to move the leg rest 102 relative to the treatment couch 101 in the x-direction 106.

In one embodiment, the motorized drive mechanism including a rack and pinion gear may be used to adjust an upper-half of a patient relative to the head-end 105 of the treatment couch 101. For example, the rack and pinion gear of FIG. 2 may be used to position the leg rest 102 in multiple positions, such as loading position 208, and treating positions 209(1)-209(N), where N is a positive integer. The motorized drive mechanism including the rack and pinion gear may position the patient to multiple treating positions 209, which allows a patient to be positioned to a specific position on the treatment couch 101 regardless of the height of the patient. For example, the head of a patient may be positioned to a treating position or mask-mounting position (as previously described) on the treatment couch 101 regardless of the height of the patient. In one embodiment, the motorized drive mechanism including the rack and pinion gear may allow the leg rest to travel up to approximately 22 inches in the x-direction 106. In another embodiment, the drive mechanism may allow the leg rest to travel up to approximately 28 inches. Alternatively, the drive mechanism may allow the leg rest to travel up to approximately 45 inches. It should be noted that this distance may be longer, depending on the length of the treatment couch 101. It should be noted, however, that in other non-treatment applications, the leg rest and corresponding drive mechanism may be designed to allow travel of the leg rest up to longer distances without departing from the scope of this invention.

The embodiments described herein may accommodate a majority of differing heights of people, such as a range from one percentile female to the ninety-nine percentile male. In one exemplary embodiment, the one percentile female to the ninety-nine percentile male is a range of approximately 58.1 to 75.6 inches. Rack and pinion gears are known by those of ordinary skill in the art, and accordingly, additional details regarding their operation and configurations have not been included so as to not obscure the embodiments of the present invention.

Figure 3:
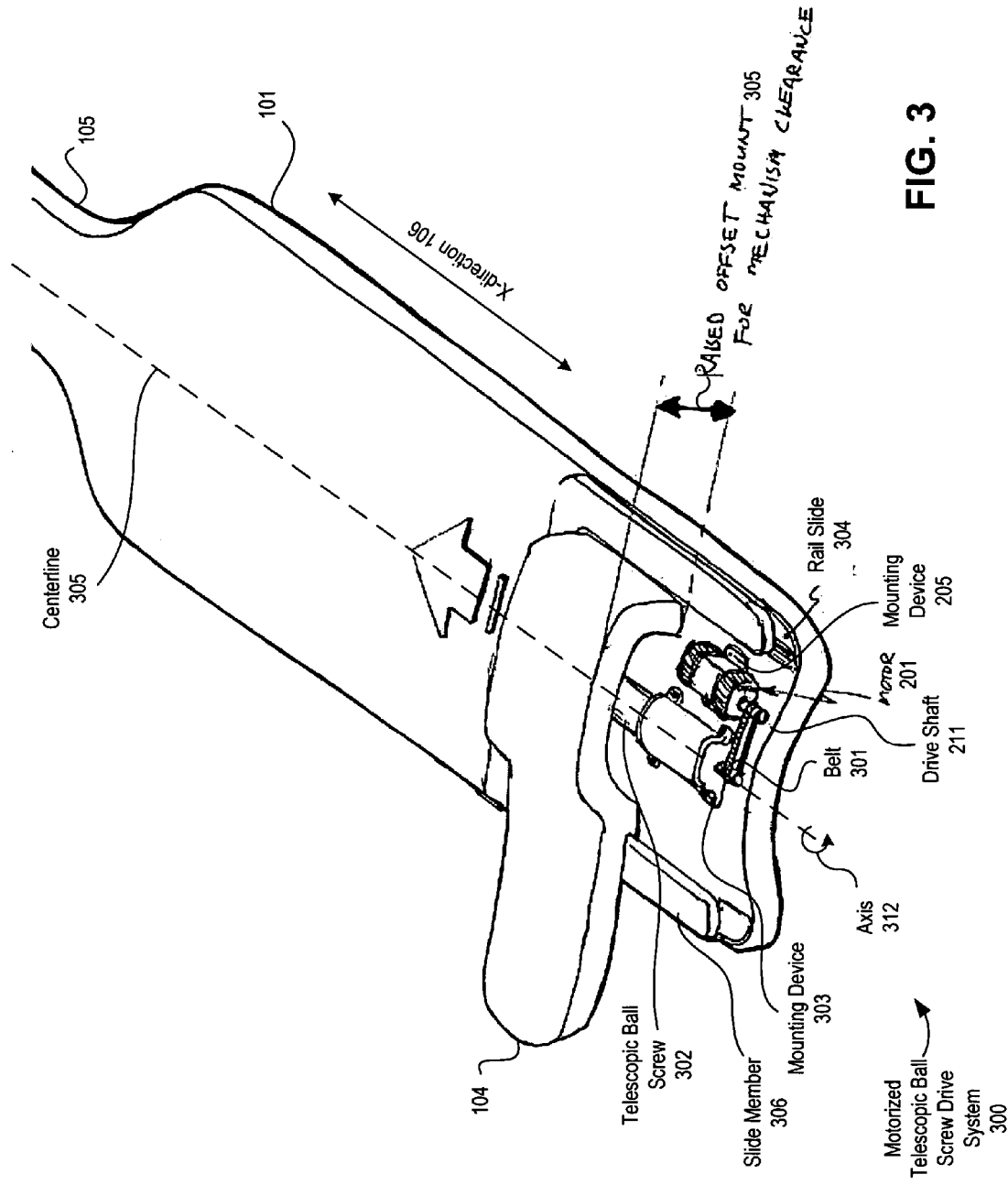
FIG. 3 illustrates one embodiment of a drive mechanism including a motorized telescopic ball screw drive system mounted on a centerline of the treatment couch.

FIG. 3 illustrates one embodiment of a drive mechanism including a motorized telescopic ball screw drive system 300 mounted on a centerline of the treatment couch. The motorized telescopic ball screw drive system includes motor 201, belt 301, and telescopic ball screw 302. The motorized telescopic ball screw drive system is used to convert rotational motion of the motor 201 about the axis 312 into linear motion of the leg rest 102 or treatment couch 101 in the x-direction 106. Motor 201 is mounted to treatment couch 101 via mounting device 205. Belt 301 is coupled to the motor 201 and the telescopic ball screw 302. The motor 201 rotates one end of the belt 301 via a drive shaft 211. The other end of the belt 301 rotates the telescopic ball screw 302. The telescopic ball screw 302 is coupled to mounting device 303. Mounting device 303 is secured to the treatment couch 101. As the telescopic ball screw 302 is rotated a portion of the telescopic ball screw 302 moves up and down relative to the head-end 105 of the treatment couch 101 in the x-direction 106. The telescopic ball screw 302 is coupled to the leg rest 102. Telescopic ball screw 302 may be coupled to the leg rest 102 by a T-shaped bracket (not illustrated) and a slide member 306. Slide member 306 moves along rail slide 304. The rail slide 304 may be used to facilitate translational motion of the leg rest 102 relative to a head-end 105 of the treatment couch 101. Rail slide 304 may be mounted to the external surface of the treatment couch 101, or alternatively, it may be embedded within the treatment couch 101, as illustrated in FIG. 3. Accordingly, as the motor 201 rotates, motor 201 drives the belt 301, which in turns drives the telescopic ball screw 302 in a linear, translational direction (e.g., 106), which in turn drives the leg rest 102 (via slide member 306 and rail slide 304) in a linear, translational direction (e.g., 106). The surface of the telescopic ball screw 302 includes grooves or threads. The motorized telescopic ball screw drive system 300 includes a ball screw nut or ball screw car. The ball screw nut includes ball bearings (e.g., recirculating channel of balls) that pass through the large grooves or threads on the telescopic ball screw 302 to facilitate motion of ball screw nut along the telescopic ball screw 302. In one exemplary embodiment, the ball screws may be ball screws manufactured by HIWIN Corporations of Mt. Prospect, Ill. In another embodiment, a linear actuator may be used instead of a telescopic ball screw drive system. Alternatively, other drive systems known by those of ordinary skill in the art may be used, such as a pneumatic cylinder, or a regular drive screw driven by a stepper motor.

In one embodiment, the drive mechanism including a motorized telescopic ball screw drive system 300 may be housed under the extension mounting area (e.g., bracket) 104. Extension mounting area 104 may include a raised offset mount 305 for clearance of the drive mechanism. In another embodiment, the drive mechanism may be embedded within the treatment couch 101 either on a centerline 305 or on an off-center line of the treatment couch 101 so that the raised offset mount 305 may not be needed for clearance of the drive mechanism. Alternatively, the drive mechanism may be mounted to the external surface of the treatment couch 101 on an off-center line so that the raised offset mount 305 may not be needed for clearance of the drive mechanism. The drive mechanism may also be mounted to the extension area 104, or alternatively, to the leg rest 102 (not illustrated in FIG. 3).

In one embodiment, the drive mechanism including a motorized telescopic ball screw drive system 300 may be used to adjust an upper-half of a patient relative to the head-end 105 of the treatment couch 101. For example, the motorized telescopic ball screw drive system 300 of FIG. 3 may be used to position the leg rest 102 in multiple positions, such as a loading position, and one or more treating positions. The drive mechanism including the motorized telescopic ball screw drive system may position the patient to multiple treating positions, which allows a patient to be positioned to a specific position on the treatment couch 101 regardless of the height of the patient. For example, the head of a patient may be positioned to a treating position or mask-mounting position (as previously described) on the treatment couch 101 regardless of the height of the patient. In one embodiment, the telescopic ball screw may allow the leg rest to travel up to approximately 45 inches in the x-direction 106. Alternatively, the drive mechanism may allow the leg rest to travel up to approximately 28 inches. The embodiments described herein may accommodate a majority of the differing heights of people, such as a range from one percentile female (e.g., 58.1 inches) to the 99 ninety-nine percentile male (e.g., 75.6 inches). Motorized telescopic ball screw drive systems are known by those of ordinary skill in the art, and accordingly, additional details regarding their operation and configurations have not been included so as to not obscure the embodiments of the present invention. Alternatively, the motorized drive mechanism may be a linear actuator, a pneumatic cylinder, a regular drive screw driven by a stepper motor, or other actuators known by those of ordinary skill in the art.

Figure 4:
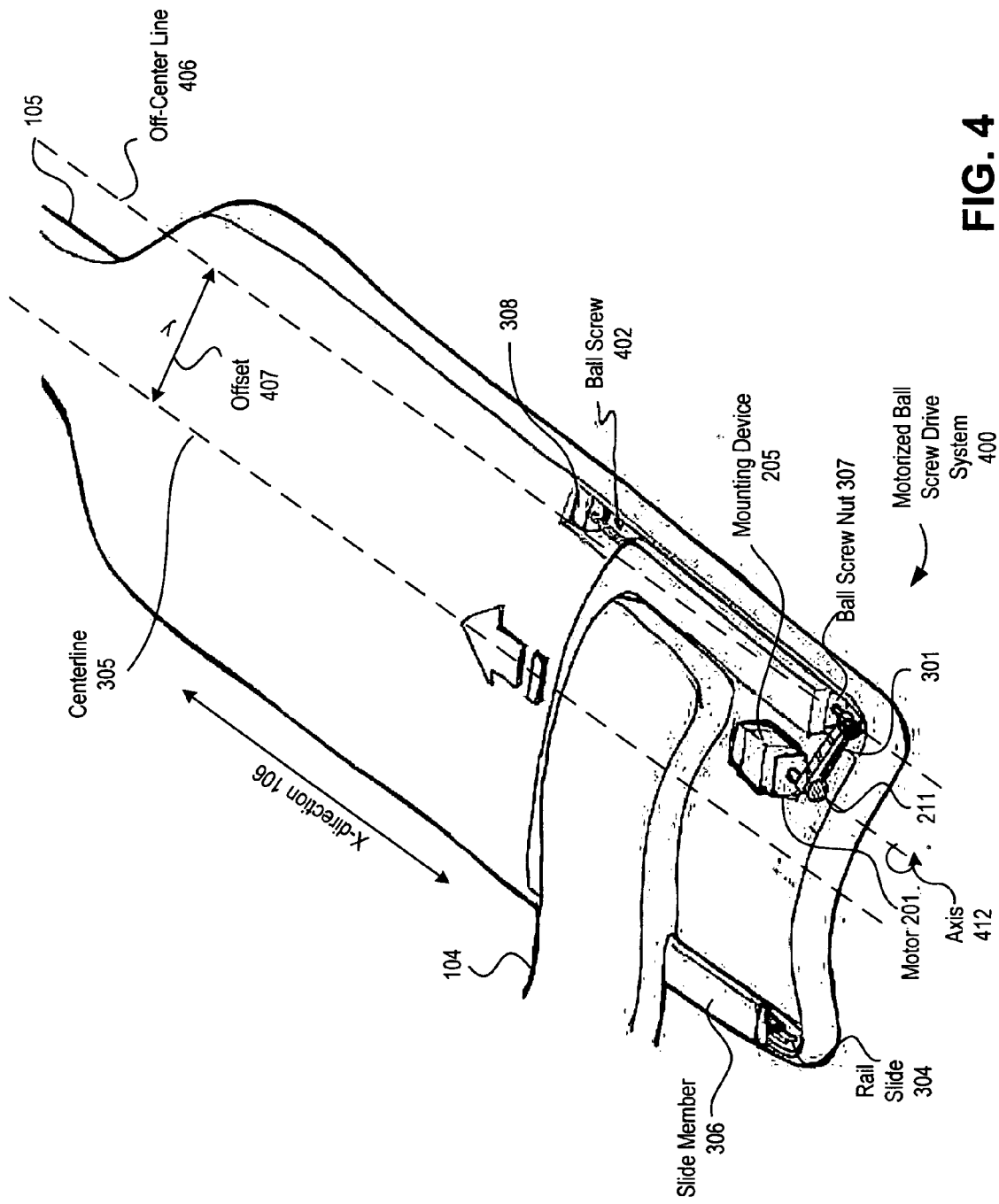
FIG. 4 illustrates one embodiment of a drive mechanism including a single motorized ball screw drive system mounted on an off-center line of the treatment couch.

FIG. 4 illustrates one embodiment of a drive mechanism including a single motorized ball screw drive system 400 mounted on an off-center line of the treatment couch. The single motorized ball screw drive system 400 includes motor 201, belt 301, ball screw 402, and ball screw nut 307. The single motorized ball screw drive system 400 is used to convert rotational motion of the motor 201 about axis 412 into linear motion of the leg rest 102 or treatment couch 101 in the x-direction 106. Motor 201 is mounted to treatment couch 101 via mounting device 205. The single ball screw 402 may include a housing, which may be mounted to the external surface of the treatment couch 101 using one or more mounting devices (e.g., 308), or alternatively, embedded within the treatment couch 101, as illustrated in FIG. 4. Alternatively, the single ball screw 402 may be mounted directly to the treatment couch 101 without the housing. A single ball screw 402 may be mounted to the treatment couch 101 on an off-center line 406 of the treatment couch 101. The off-center line 406 may be an offset distance 407 from the centerline 305 of the treatment couch 101. In one exemplary embodiment, the offset distance 407 may have a range of approximately zero to approximately twelve inches from the centerline 305. Alternatively, other offsets may be used. The single ball screw 402 is coupled to slide member 306 via ball screw nut 307. Belt 301 is coupled to the motor 201 and the single ball screw 402. The motor 201 rotates one end of the belt 301 via a drive shaft 211. The other end of the belt 301 rotates the single ball screw 402.

Ball screw nut 307 includes a hole in which the single ball screw 402 passes. The surface of the ball screw 402 include grooves or threads, and the ball screw nut 307 includes ball bearings (e.g., recirculating channel of balls) that pass through the grooves or threads of the ball screw 402 to facilitate motion of ball screw nut 307 along the single ball screw 402. It should be noted that the ball bearings of the ball screw nut 307 are smaller than the grooves of the ball screw 402. As the single ball screw 402 is rotated by motor 201 via belt 301, ball screw nut 307 moves along the single ball screw 402 relative to the head-end 105 of the treatment couch 101 in the x-direction 106. Ball screw nut 307 is coupled to slide member 306, which is coupled to the leg rest 102. As the ball screw nut 307 moves along the single ball screw 402, the leg rest 102 moves up and down along the one translational direction, x-direction 106, relative to the head-end 105 of the treatment couch 101, via slide member 306. In other words, as the motor 201 rotates, motor 201 drives the belt 301, which in turns rotates the single ball screw 402, which in turn drives the ball screw nut 307 in a linear, translational direction (e.g., 106), which in turn drives the leg rest 102 (via slide member 306) in a linear, translational direction (e.g., 106). In another embodiment, a regular drive screw may be used in place of the ball screw. The regular drive screw and corresponding nut or car includes threads to facilitate motion of the nut or car along the screw. Alternatively, other actuators known by those of ordinary skill in the art may be used in this configuration, such as a linear actuator, a pneumatic cylinder, a regular drive screw driven by a stepper motor.

It should be noted that due to the fact that the forces in the off-center line mounting (e.g., off-center line 406) may be higher than forces in the centerline mounting (e.g., center line 305), the size of the drive mechanism and slide member may need to be increased to compensate or overcome the offset imbalance. By using two drives in parallel, the sizing of lead screws (e.g., ball screws) may be reduced, as described below with respect to FIG. 5.

In one embodiment, the drive mechanism including a single motorized ball screw 402 may be used to adjust an upper-half of a patient relative to the head-end 105 of the treatment couch 101. For example, the single motorized ball screw 402 of FIG. 4 may be used to position the leg rest 102 in multiple positions, such as a loading position, and one or more treating positions. The drive mechanism including the single motorized ball screw may position the patient to multiple treating positions, which allows a patient to be positioned to a specific position on the treatment couch 101 regardless of the height of the patient. For example, the head of a patient may be positioned to a treating position or mask-mounting position (as previously described) on the treatment couch 101 regardless of the height of the patient. In one embodiment, the drive mechanism including the offset single ball screw may allow the leg rest to travel up to approximately 22 inches in the x-direction 106. In another embodiment, the drive mechanism may allow the leg rest to travel up to approximately 28 inches. Alternatively, the drive mechanism may allow the leg rest to travel up to approximately 45 inches. It should be noted that this distance may be longer, depending on the length of the treatment couch 101. It should be noted, however, that in other non-treatment applications, the leg rest and corresponding drive mechanism may be designed to allow travel of the leg rest up to longer distances without departing from the scope of this invention.

The embodiments described herein may accommodate a majority of differing heights of people, such as a range from one percentile female (e.g., 58.1 inches) to the ninety-nine percentile male (e.g., 75.6 inches). Motorized ball screws are known by those of ordinary skill in the art, and accordingly, additional details regarding their operation and configurations have not been included so as to not obscure the embodiments of the present invention.

Figure 5:
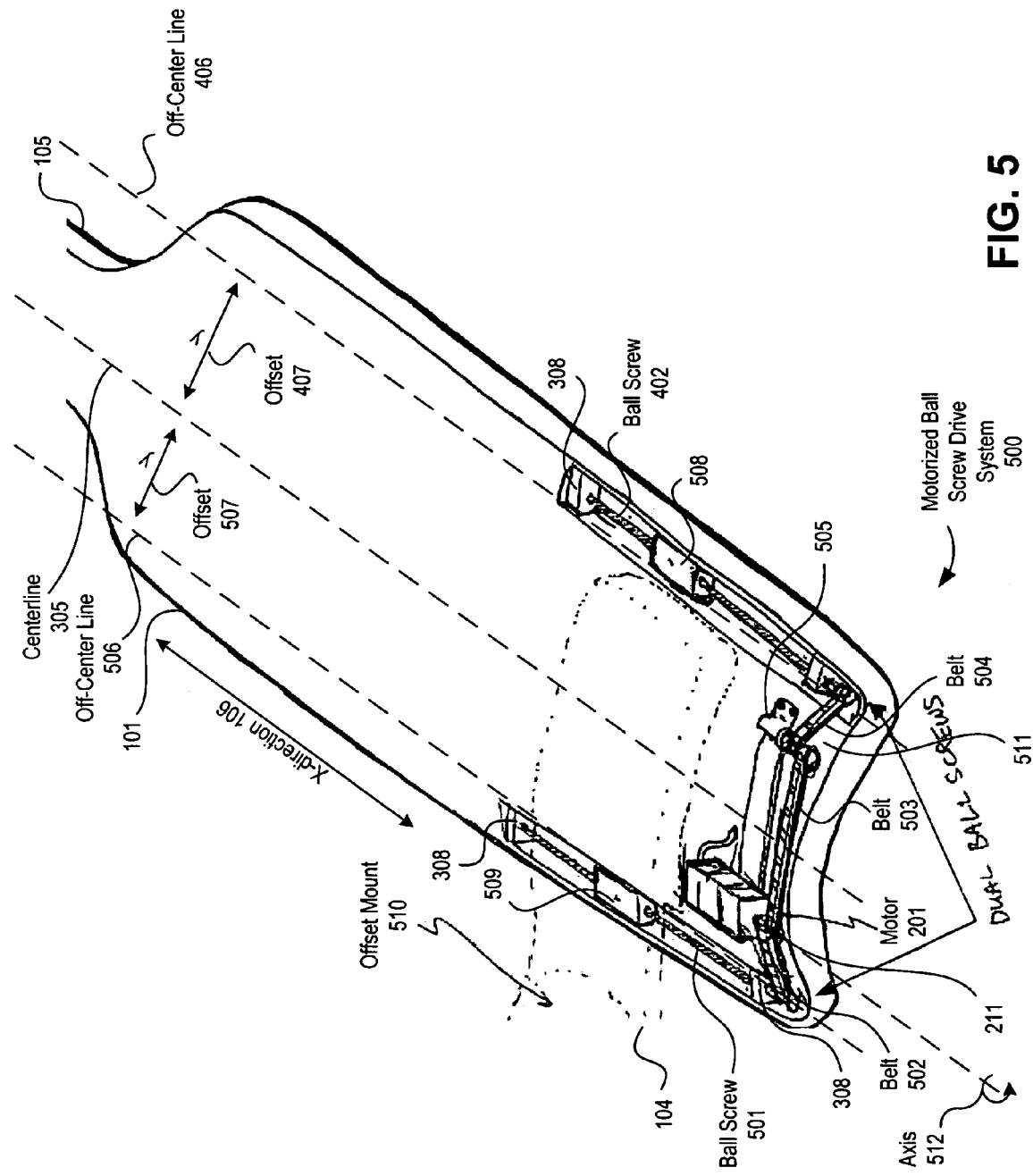
FIG. 5 illustrates one embodiment of a drive mechanism including dual motorized ball screw drive system, including one motor, mounted on off-center lines of the treatment couch.

FIG. 5 illustrates one embodiment of a drive mechanism including dual motorized ball screw drive system 500, including one motor, mounted on off-center lines of the treatment couch. The dual motorized ball screw drive system 500 includes motor 201, belts 502, 503, and 504, ball screw 402 and 501, and ball screw nuts 508 and 509. The dual motorized ball screw drive system 500 is used to convert rotational motion of the motor 201 about the axis 512 into linear motion of the leg rest 102 or treatment couch 101 in the x-direction 106. Motor 201 is mounted to treatment couch 101 via mounting device 505. Mounting device 505 may include an additional drive shaft 511, to translate the rotation of belt 503 to belt 504. Belt 502 is coupled to the ball screw 501 and the motor 201 (e.g., drive shaft 211). Belt 503 is coupled to the motor 201 (e.g., drive shaft 211), and the additional drive shaft 511. Belt 504 is coupled to belt 503, via the additional drive shaft 511, and to ball screw 402. The motor 201 rotates one end of the belts 502 and 503 via drive shaft 211. The other end of belt 502 rotates the ball screw 501. The other end of belt 503 rotates the additional drive shaft 511. The additional drive shaft 511 rotates one end of the belt 504. The other end of belt 504 rotates the ball screw 402.

The dual ball screws (e.g., 402 and 501) may be mounted to the treatment couch 101 on off-center lines 406 and 506 of the treatment couch 101. The off-center line 406 may be a first offset distance 407 from the centerline 305 of the treatment couch 101. The offset line 506 may be a second offset distance 507 from the centerline 305 of the treatment couch 101. In one exemplary embodiment, the offset distances 407 and 507 may have a range of approximately zero to approximately twelve inches from the centerline 305. Alternatively, other offset distances may be used. The dual ball screws 402 and 501 may be mounted to the external surface of the treatment couch 101 using mounting device 308. Alternatively, as illustrated in FIG. 5, the dual ball screws 402 and 501 and their corresponding assemblies may be embedded within the treatment couch 101 using mounting device 308.

Ball screw nuts 508 and 509 include a hole in which the ball screws pass. The surface of the ball screw (e.g., 402 and 501)

include grooves or threads, and the ball screw nuts (e.g., 508 and 509) include ball bearings (e.g., recirculating channel of balls) that pass through the grooves or threads of the ball screws 402 and 501 to facilitate motion of the ball screw nut along the ball screw. As the ball screws are rotated by motor 201 via belts 502, 503, and 504, ball screw nuts 508 and 509 move along the dual ball screw 402 and 501 relative to the head-end 105 of the treatment couch 101 in the x-direction 106. Ball screw nuts 508 and 509 are coupled to a slide member 306, which is coupled to the leg rest 102. As the ball screw nuts 508 and 509 move along the dual ball screws 402 and 501, the leg rest 102 moves up and down along the one translational direction, x-direction 106, relative to the head-end 105 of the treatment couch 101, via slide member 306. In other words, as the motor 201 rotates, motor 201 drives the belts, which in turns rotates the ball screws, which in turn drive the cars in a linear, translational direction (e.g., 106), which in turn drives the leg rest 102 in a linear, translational direction (e.g., 106). In another embodiment, a regular drive screw may be used in place of the ball screw. The regular drive screw and corresponding nut or car includes threads to facilitate motion of the nut or car along the screw. Alternatively, other actuators known by those of ordinary skill in the art may be used in this configuration, such as a linear actuator, a pneumatic cylinder, a regular drive screw driven by a stepper motor.

As previously described, due to the fact that the forces in the off-center line mounting may be higher than forces in the centerline mounting, the size of the drive mechanism and slide member may need to be increased to compensate or overcome the offset imbalance. By using two drives (e.g., ball screws) in parallel, the sizing of lead screws (e.g., ball screws) may be reduced. Using two drives in parallel may also result in reduced loads due to the lack of resulting moments. Using two drives may allow other components of the drive mechanism to be reduced, such as the slide member 306, mounting devices 205 and 308. In one embodiment, the ball screw(s) may by driven by one motor with connecting belt(s). Alternatively, the ball screws(s) may be driven by two stepper motors. These stepper motors may be synchronized stepper motors. As previously mentioned, the ball screws may be regular drive screws driven by stepper motors, a linear actuator, a pneumatic cylinder, or other actuators known by those of ordinary skill in the art.

In one embodiment, the drive mechanism including dual motorized ball screws 402 and 501 may be used to adjust an upper-half of a patient relative to the head-end 105 of the treatment couch 101. For example, the dual motorized ball screws 402 and 501 of FIG. 5 may be used to position the leg rest 102 in multiple positions, such as a loading position, and one or more treating positions. The drive mechanism including the single motorized ball screw may position the patient to multiple treating positions, which allows a patient to be positioned to a specific position on the treatment couch 101 regardless of the height of the patient. For example, the head of a patient may be positioned to a treating position or mask-mounting position (as previously described) on the treatment couch 101 regardless of the height of the patient. In one embodiment, the drive mechanism including the dual motorized ball screws may allow the leg rest to travel up to approximately 24 inches in the x-direction 106. In another embodiment, the drive mechanism may allow the leg rest to travel up to approximately 28 inches. Alternatively, the drive mechanism may allow the leg rest to travel up to approximately 45 inches. It should be noted that this distance may be longer, depending on the length of the treatment couch 101. It should be noted, however, that in other non-treatment applications, the leg rest and corresponding drive mechanism may be designed to allow travel of the leg rest up to longer distances without departing from the scope of this invention.

The embodiments described herein may accommodate a majority of the differing heights of people, such as a range from one percentile female (e.g., 58.1 inches) to the ninety-nine percentile male (e.g., 75.6 inches). Motorized ball screws are known by those of ordinary skill in the art, and accordingly, additional details regarding their operation and configurations have not been included so as to not obscure the embodiments of the present invention.

Figure 6A:
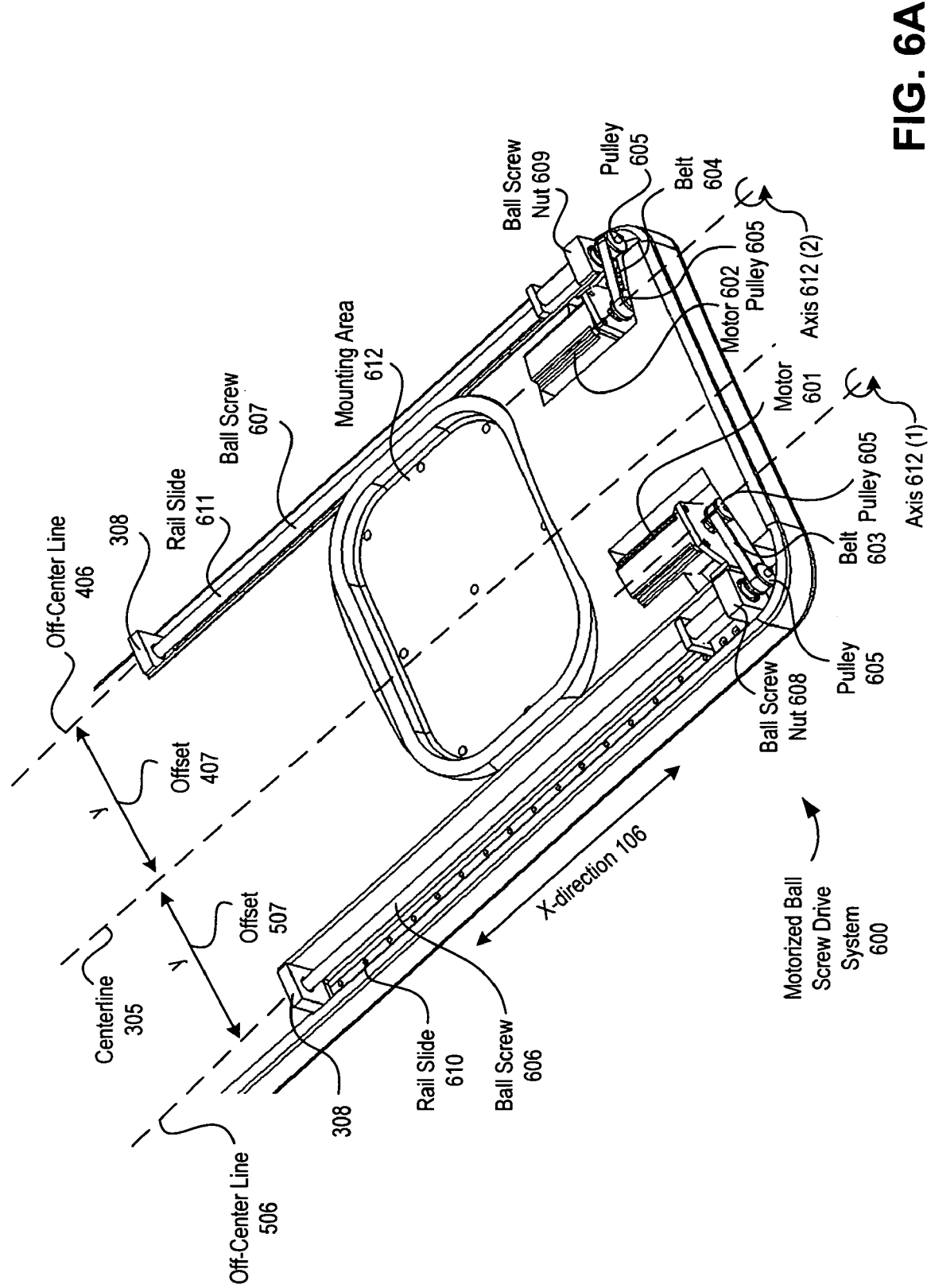
FIG. 6A illustrates another embodiment of a drive mechanism including dual motorized ball screw drive system, including two motors, mounted on off-center lines of the treatment couch.

FIG. 6A illustrates another embodiment of a drive mechanism including dual motorized ball screw drive system 600, including two motors, mounted on off-center lines of the treatment couch. The dual motorized ball screw drive system 600 of FIG. 6A includes motors 601 and 602, belts 603 and 604, multiple pulleys 605, ball screw 606 and 607, and cars 608 and 609. The dual motorized ball screw drive system 600 is used to convert rotational motion of the motors 601 and 602 about axis 612(1) and axis 612(2) into linear motion of the leg rest 102 or treatment couch 101 in the x-direction 106. Motors 601 and 602 are embedded within treatment couch 101. Alternatively, motors 601 and 602 may be mounted to the external surface of the treatment couch 101. Belts 603 and 604 are coupled to the motors 601 and 602, respectively. Pulleys, such as pulley 605, may be used to couple the motors and belts. For example, pulley 605 may be coupled to a drive shaft that extends from the motors 601 and 602. Alternatively, the belts may couple directly to the motor. Belts 603 and 604 are coupled to ball screws 606 and 607, respectively. Pulleys, such as pulley 605, may also be used to couple the belts and the ball screws 606 and 607. For example, pulley 605 may be coupled to end of the ball screws 606 and 607 and the belts 603 and 604. Alternatively, the belts may couple directly to the ball screws. In one embodiment, belts 603 and 604 may include teeth to prevent the ball screw from slipping.

Motors 601 and 602 rotate one end of the belts 603 and 604 via drive shafts and pulleys. The other end of belt 603 rotates the ball screw 606. The other end of belt 604 rotates the ball screw 607. The dual ball screws (e.g., 606 and 607) may be mounted to the treatment couch 101 on off-center lines 406 and 506 of the treatment couch 101. The offset line 406 may be a first offset distance 407 from the centerline 305 of the treatment couch 101. The offset line 506 may be a second offset distance 507 from the centerline 305 of the treatment couch 101. In one exemplary embodiment, the offset distances 407 and 507 may have a range of approximately zero to approximately twelve inches from the centerline 305. Alternatively, other offset distances may be used. The dual ball screws 606 and 607 may be mounted to the external surface of the treatment couch 101 using mounting device 308. Alternatively, as illustrated in FIG. 5, the dual ball screws 606 and 607 and their corresponding assemblies may be embedded within the treatment couch 101 using mounting device 308.

In one embodiment, the motors 601 and 602 are stepper motors. Alternatively, other motors known by those of ordinary skill in the art may be used, such as servomotors or other additional motors with encoders. Motors 601 and 602 may also be synchronized. The stepper motors may run open loop. In another embodiment, brakes may be applied to the motors to stop the leg rest in the event of a power failure or in response to an operator command.

Ball screw nuts 608 and 609 include a hole in which the ball screws pass. The surface of the ball screws (e.g., 606 and 607) include grooves or threads, and the ball screw nuts (e.g., 608 and 609) include ball bearings (e.g., recirculating channel of balls) that pass through the grooves or threads of the ball screws 606 and 607 to facilitate motion of the ball screw nut along the ball screw. As the ball screws 606 and 607 are rotated by motors 601 and 602 via belts 603 and 604, and pulleys 605, cars 608 and 609 move along the dual ball screw 606 and 607 relative to the head-end 105 of the treatment couch 101 in the x-direction 106. Ball screw nuts 608 and 609 may be coupled to a slide member 306, which is coupled to the leg rest 102. Alternatively, ball screw nuts 608 and 609 may be coupled directly to the leg rest 102. As the ball screw nuts 608 and 609 move along the dual ball screws 606 and 607, the leg rest 102 moves up and down along the one translational direction, x-direction 106, relative to the head-end 105 of the treatment couch 101 (e.g., via slide member 306). In other words, as the motor rotates, the motor drives the belt, which in turns rotates the ball screw, which in turn drives the car in a linear, translational direction (e.g., 106), which in turn drives the leg rest 102 in a linear, translational direction (e.g., 106). In another embodiment, a regular drive screw may be used in place of the ball screw. The regular drive screw and corresponding nut or car includes threads to facilitate motion of the nut or car along the screw. Alternatively, other actuators known by those of ordinary skill in the art may be used in this configuration, such as a linear actuator, a pneumatic cylinder, a regular drive screw driven by a stepper motor.

The drive mechanisms of FIG. 6A also includes two rail slides 610 and 611. Rail slides 610 and 611 may be used to guide the cars 608 and 609 along the ball screws 606 and 607. In another embodiment, the drive mechanism may include rail slides and linear guides to facilitate the linear motion of the cars along the ball screws.

As previously described, due to the fact that the forces in the off-center line mounting may be higher than forces in the centerline mounting, the size of the drive mechanism and slide member may need to be increased to compensate or overcome the offset imbalance. By using two drives (e.g., ball screws) in parallel, the sizing of lead screws (e.g., ball screws) may be reduced. Using two drives in parallel may also result in reduced loads due to the lack of resulting moments. Using two drives may allow other components of the drive mechanism to be reduced, such as the slide member 306, mounting devices 205 and 308. In one embodiment, the ball screw(s) may by driven by one motor with connecting belt(s). Alternatively, the ball screws(s) may be driven by two stepper motors, as illustrated in FIG. 6A. These stepper motors may be synchronized stepper motors. As previously mentioned, the ball screws may be regular drive screws driven by stepper motors, a linear actuator, a pneumatic cylinder, or other actuators known by those of ordinary skill in the art.

In one embodiment, the drive mechanism including dual motorized ball screws 606 and 607 may be used to adjust an upper-half of a patient relative to the head-end 105 of the treatment couch 101. For example, the dual motorized ball screws 606 and 607 of FIG. 6A may be used to position the leg rest 102 in multiple positions, such as a loading position, and one or more treating positions. The drive mechanism including the single motorized ball screw may position the patient to multiple treating positions, which allows a patient to be positioned to a specific position on the treatment couch 101 regardless of the height of the patient. For example, the head of a patient may be positioned to a treating position or mask-mounting position (as previously described) on the treatment couch 101 regardless of the height of the patient.

In one embodiment, the drive mechanism including the dual motorized ball screws may allow the leg rest to travel up to approximately 24 inches in the x-direction 106. In another embodiment, the drive mechanism may allow the leg rest to travel up to approximately 28 inches. Alternatively, the drive mechanism may allow the leg rest to travel up to approximately 45 inches. It should be noted that this distance may be longer, depending on the length of the treatment couch 101. It should be noted, however, that in other non-treatment applications, the leg rest and corresponding drive mechanism may be designed to allow travel of the leg rest up to longer distances without departing from the scope of this invention.

The embodiments described herein may accommodate a majority of differing heights of people, such as a range from one percentile female (e.g., 58.1 inches) to the ninety-nine percentile male (e.g., 75.6 inches). Motorized ball screws are known by those of ordinary skill in the art, and accordingly, additional details regarding their operation and configurations have not been included so as to not obscure the embodiments of the present invention.

The treatment couch 101 of FIG. 6A includes a mounting area 612. Mounting area 612 may be used to mount the treatment couch 101 to a stand, a robotic arm, or to other motorized mechanisms known by those of ordinary skill in the art to support and/or position a patient. In one embodiment, a mounting extension area (e.g., 104) may be coupled to the mounting area 612, as described below with respect to FIG. 6B.

Figure 6B:
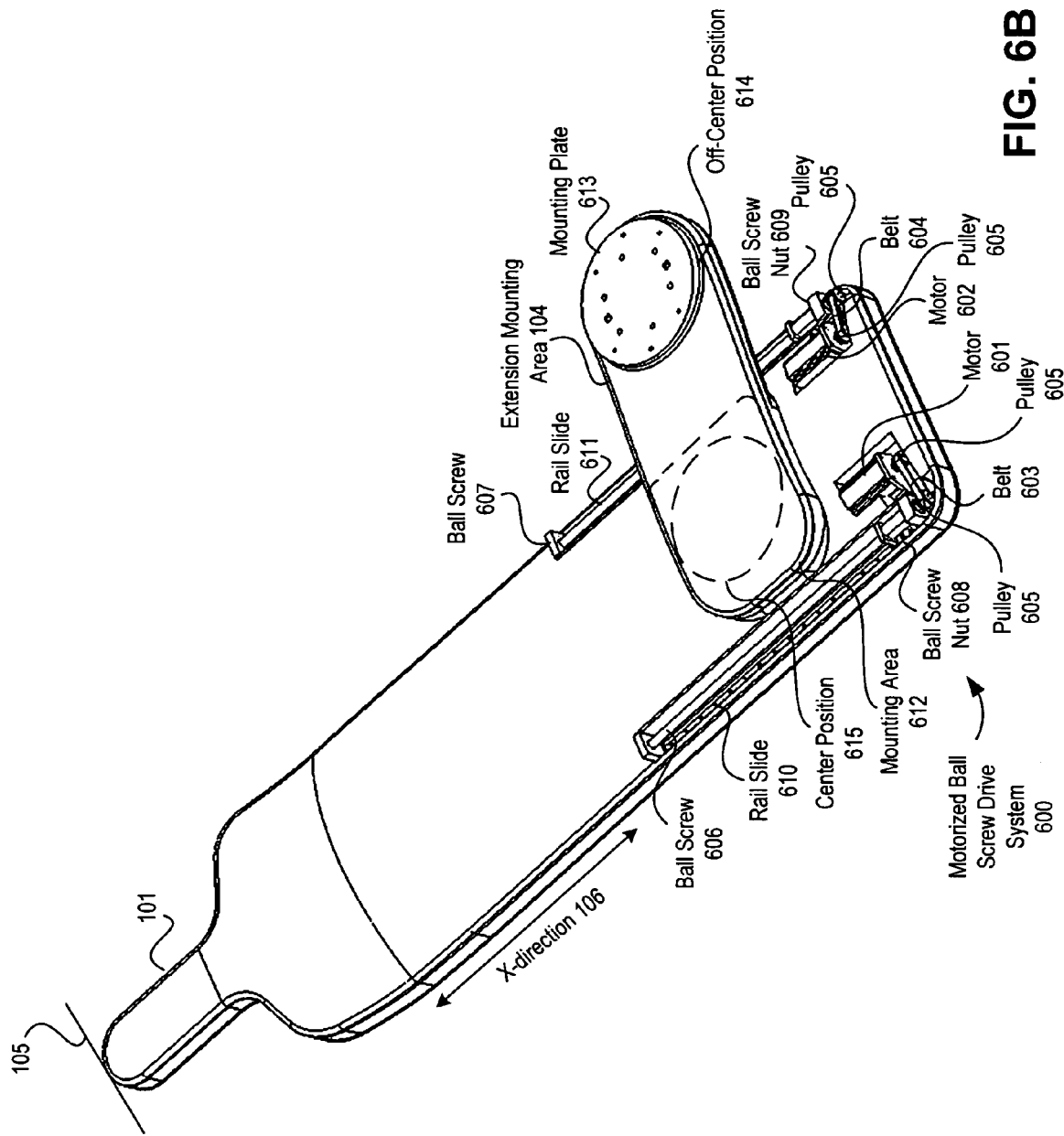
FIG. 6B illustrates the drive mechanism of FIG. 6A including an extension mounting area.

FIG. 6B illustrates the drive mechanism of FIG. 6A including an extension mounting area. The treatment couch 101 of FIG. 6B includes a mounting area 612. In one embodiment, extension mounting area 104 is mounted to the mounting area 612. Extension mounting area 104 may be used to attach mounting plate 613 at an off-center position 614. Alternatively, mounting plate 613 may be coupled to the mounting area 612 at a center position 615. In one embodiment, mounting plate 613 is coupled to a robotic arm having multiple degrees of freedom. Alternatively, the mounting plate 613 may be coupled to a stand or to a motorized mechanism for positioning a patient, or other known equipment known by those of ordinary skill in the art used to support and/or position a patient.

It should be noted that the drive mechanisms of the embodiments described herein may be controlled by a controller. The controller may be a manual mechanical controller, an electronic controller, or a computerized controller. The controller may be a hand crank, a hand controller (e.g., a hand-held pendant or remote control), or other controllers known by those of ordinary skill in the art. In one exemplary embodiment, the controller may be the controller of a robotic arm having multiple degrees of freedom, and in essence, the translational motion of the leg rest 102 becomes an additional degree of freedom or axis of articulation. Alternatively, the leg rest 102 may be controlled by other motorized mechanisms known by those of ordinary skill in the art.

Figure 7B:
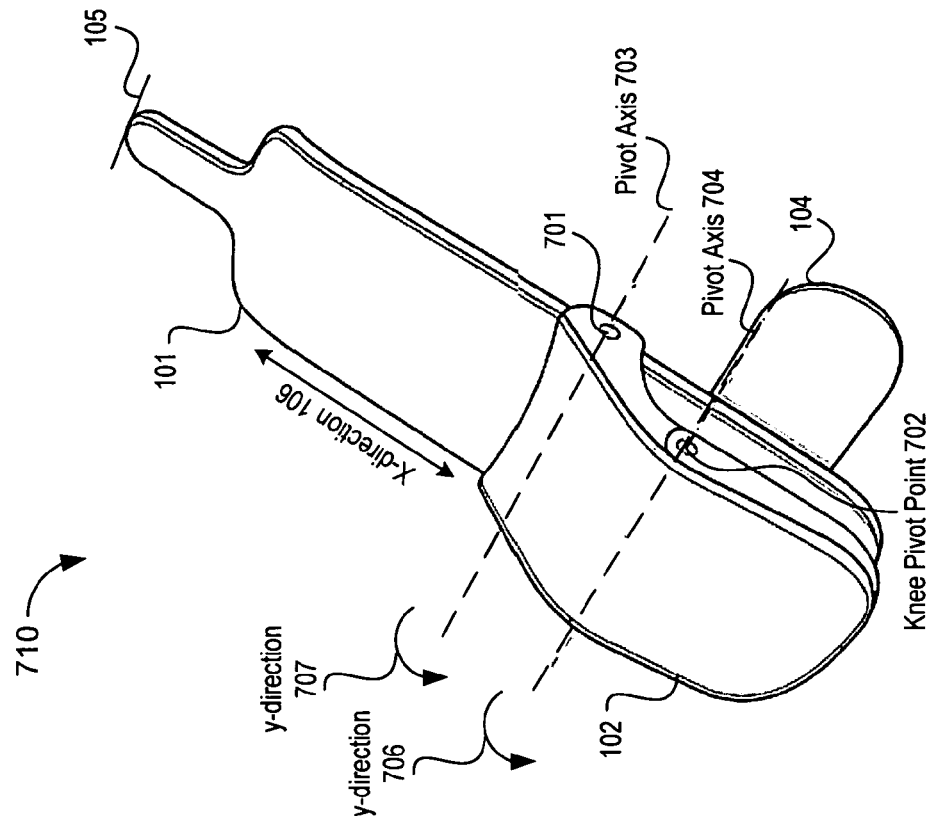
FIG. 7B illustrates another embodiment of a treatment couch including a leg rest with two pivot points.
Figure 7A:
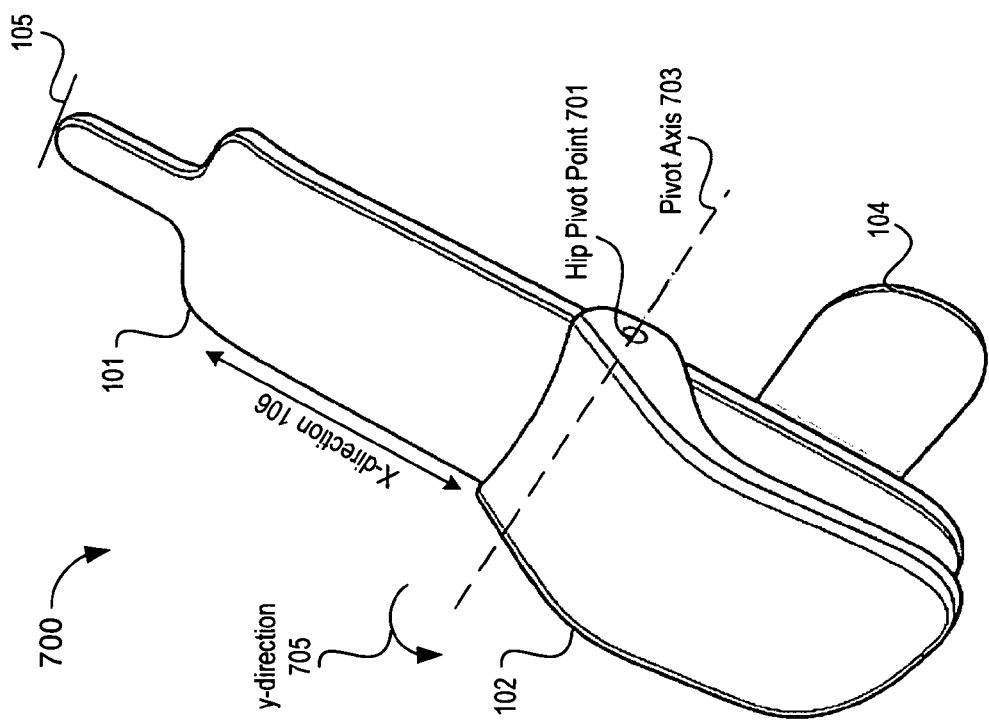
FIG. 7A illustrates one embodiment of a treatment couch including a leg rest with one pivot point.

FIG. 7A illustrates one embodiment of a treatment couch including a leg rest with one pivot point. Patient positioning system 700 includes treatment couch 101, leg rest 102, and extension mounting area 104. Treatment couch 101 is coupled to the leg rest 102 and extension mounting area 104. In one embodiment, leg rest 102 includes one pivot point, such as hip pivot point 701. Hip pivot point 701 facilitates a rotational motion (e.g., tilting motion) of the leg rest 102. The leg rest 102 supports the lower-half of the patient's body while loading and treating the patient. The leg rest 102 may move in a y-rotational direction 705 about the pivot axis 703. Leg rest 102 may also be coupled to a drive mechanism (e.g., 103) to facilitate translational motion (e.g., sliding or lifting motion) in the x-direction 106, as in other embodiments described herein. The tilting motion of the leg rest 102 in the y-rotational direction 705 about pivot axis 703 may be caused manually or motorized. For example, the leg rest 102 may be coupled to a motorized mechanism, such as a motor or gearbox. Alternatively, the tilting motion may be done manually by an operator, such as with a non-motorized mechanical device (e.g., hand crank) or using his/her hands.

In one embodiment, a manual mechanical controller may be used to move the leg rest in a translational direction, such as a manual ratchet device, similar to those found in folding chaises of a lounge chair. As the leg rest is rotated upwards, it locks at set intervals. The leg rest may need to be rotated to its extreme in order to be reset. In another embodiment, an electronic button or buttons may be placed on the side of the leg rest. The electronic button(s) may be directly wired to the motors to control the movement of the leg rest. Alternatively, other non-computerized (e.g., manual and/or electronic) controllers known by those of ordinary skill in the art may be used.

In one embodiment, a computerized mechanical controller may be used to move the leg rest in a translational direction. The motor(s) may be wired back to a computerized controller that could manipulate the pivot points as additional axes. In one embodiment, the leg rest 102 may be coupled to a controller, and the controller may control the rotation (e.g., tilting motion) of the leg rest 102 about pivot axis 703 via a motorized mechanism, such as a gearbox. In one exemplary embodiment, the controller may be the controller of a robotic arm that is coupled to the treatment couch, and the rotations of the pivot point(s) may be additional axis or axes of the robotic arm for positioning a patient, both on the treatment couch and within a treatment room with respect to a radiation source. Alternatively, other computerized controller known by those of ordinary skill in the art may be used.

FIG. 7B illustrates another embodiment of a treatment couch including a leg rest with two pivot points. Patient positioning system 710 includes treatment couch 101, leg rest 102, and extension mounting area 104. Treatment couch 101 is coupled to the leg rest 102 and extension mounting area 104. In one embodiment, leg rest 102 includes two pivot points, such as hip pivot point 701 and knee pivot point 702. Hip pivot point 701 facilitates a first rotational motion (e.g., tilting motion) of the leg rest 102. Knee pivot point 702 facilitates a second rotational motion (e.g., titling motion) of the leg rest 102. The leg rest 102 supports the lower-half of the patient's body while loading and treating the patient. The leg rest 102 may move in a first y-rotational direction 707 about the pivot axis 703 and in a second y-rotational direction 706 about the pivot axis 704. Leg rest 102 may also be coupled to a drive mechanism (e.g., 103) to facilitate translational motion (e.g., sliding or lifting motion) in the x-direction 106, as in other embodiments described herein. The tilting motion of the leg rest 102 in the z-direction 707 and 706 about pivot axes 703 and 704, respectively, may be caused manually or motorized. For example, the leg rest 102 may be coupled to a motorized mechanism, such as a motor or gearbox. Alternatively, the tilting motion may be done manually by an operator, such as with a non-motorized mechanical device (e.g., hand crank) or using his/her hands. In one exemplary embodiment, the leg rest 102 may be coupled to a controller, and the controller may control the rotation (e.g., tilting motion) of the leg rest 102 about pivot axes 703 and 704 via a motorized mechanism, such as a gearbox. It should be noted that although the leg rest illustrated in FIG. 7B includes two pivot points, alternatively, more than two pivot points may be used.

Figure 7C:
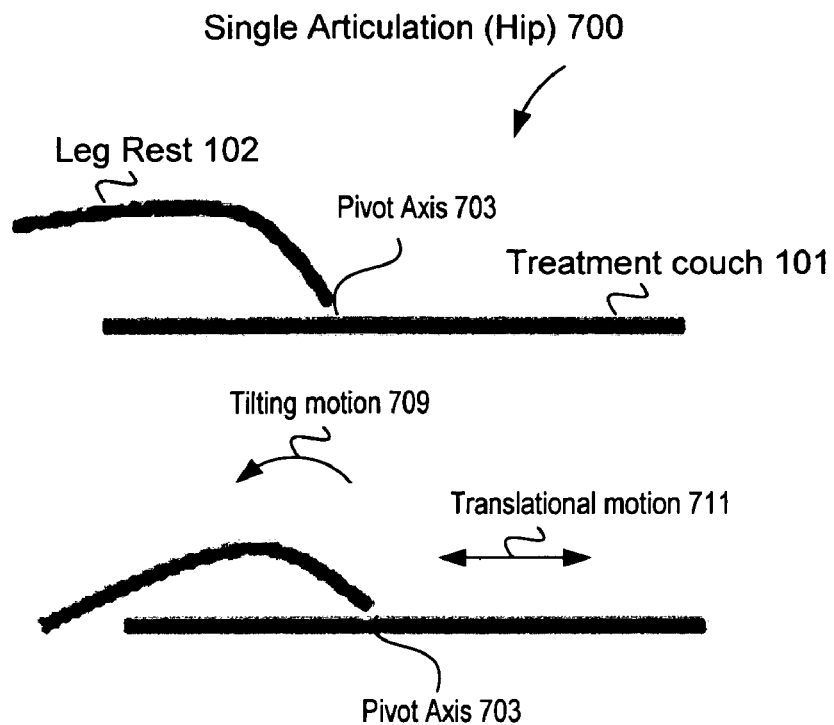
FIGS. 7C illustrates a single articulation of the one pivot point of the embodiment of FIG. 7A.

FIGS. 7C illustrates a single articulation of the one pivot point of the embodiment of FIG. 7A. The leg rest 102 of FIG. 7A includes one pivot point 701, which rotates about pivot axis 703. The single articulation 700 of the one pivot point 701 allows the leg rest 102 to move in a rotational direction, tilting motion 709, about pivot axis 703. In another embodiment, the leg rest 102 may move in the tilting motion 709 and in a translational motion 711 relative to the head-end of the treatment couch 101. The single articulation 700 of FIG. 7C may include a motorized or manual pivot point to move the leg rest 102 in tilting and translational motions 709 and 711, respectively.

Figure 7D:
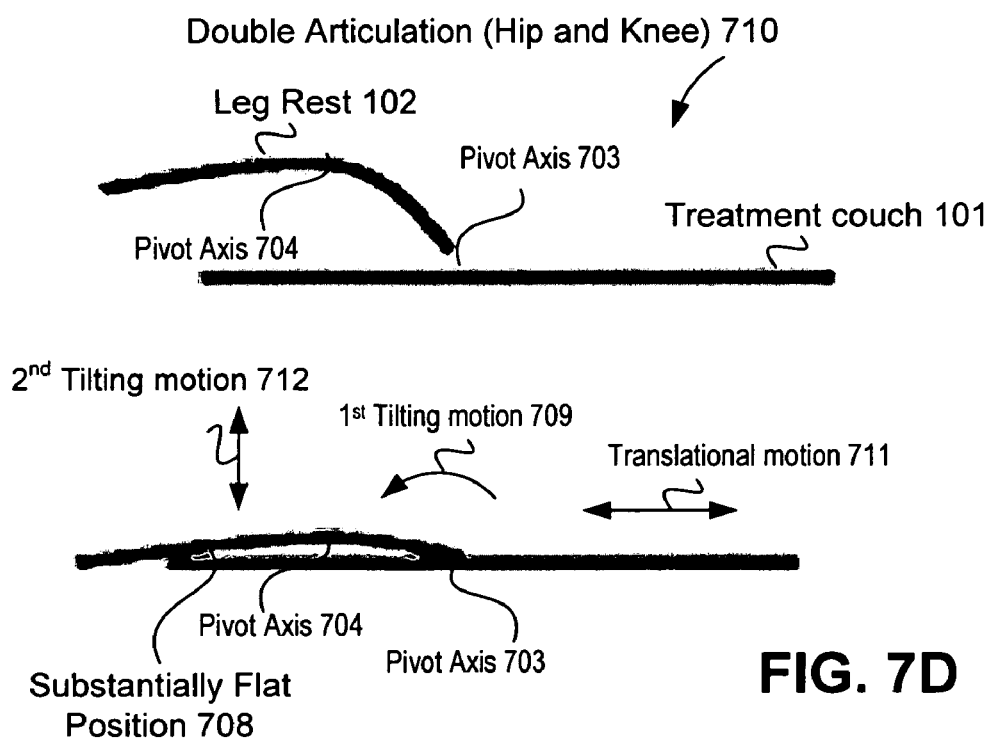
FIG. 7D illustrates a double articulation of the two pivot points of the embodiment of FIG. 7B.

FIG. 7D illustrates a double articulation of the two pivot points of the embodiment of FIG. 7B. The leg rest 102 of FIG. 7B includes two pivot points 701 and 702, which rotate about pivot axis 703 and pivot axis 704, respectively. The double articulation 710 of the two pivot points 701 and 702 allow the leg rest 102 to move in two rotational directions, first and second tilting motions 709 and 712, about pivot axes 703 and 704. In another embodiment, the leg rest 102 may move in the first and second tilting motions 709 and 712, and in a translational motion 711 relative to the head-end of the treatment couch 101. The double articulation 710 of FIG. 7D may include motorized or manual pivot points to move the leg rest 102 in the first and second tilting and translational motions 709, 712, and 711, respectively.

In one embodiment, the first and second tilting motions 709 and 710 about pivot axes 703 and 704 may be independent motions. Alternatively, the second tilting motion 710 may follow the first tilting motion through a linkage. The linkage may be a rigid link between the two parts of the leg rest that move and may be used to keep a portion of the leg rest, which is below the knee pivot, at a fixed angle relative to the table top while the angle of a second portion of the leg rest, which is above the knee pivot, is rotating about pivot axis 703. In one embodiment, the dual articulation 710, having two pivot points, may be used to flatten the leg rest 102 with respect to the plane of the treatment couch 101. In other words, the double articulation 710, having two pivot points 701 and 702, may permit the leg rest 102 to be positioned substantially flat with respect to a plane of a top surface of the treatment couch 102 in substantially flat position 708. This may allow the leg rest 102 to remain attached to the treatment couch 101 during prone treatments of which, normally, the leg rest 102 would be removed. For example, in prone treatments the leg rest at pivot point 702 may push right into the patient's knees.

Figure 8:
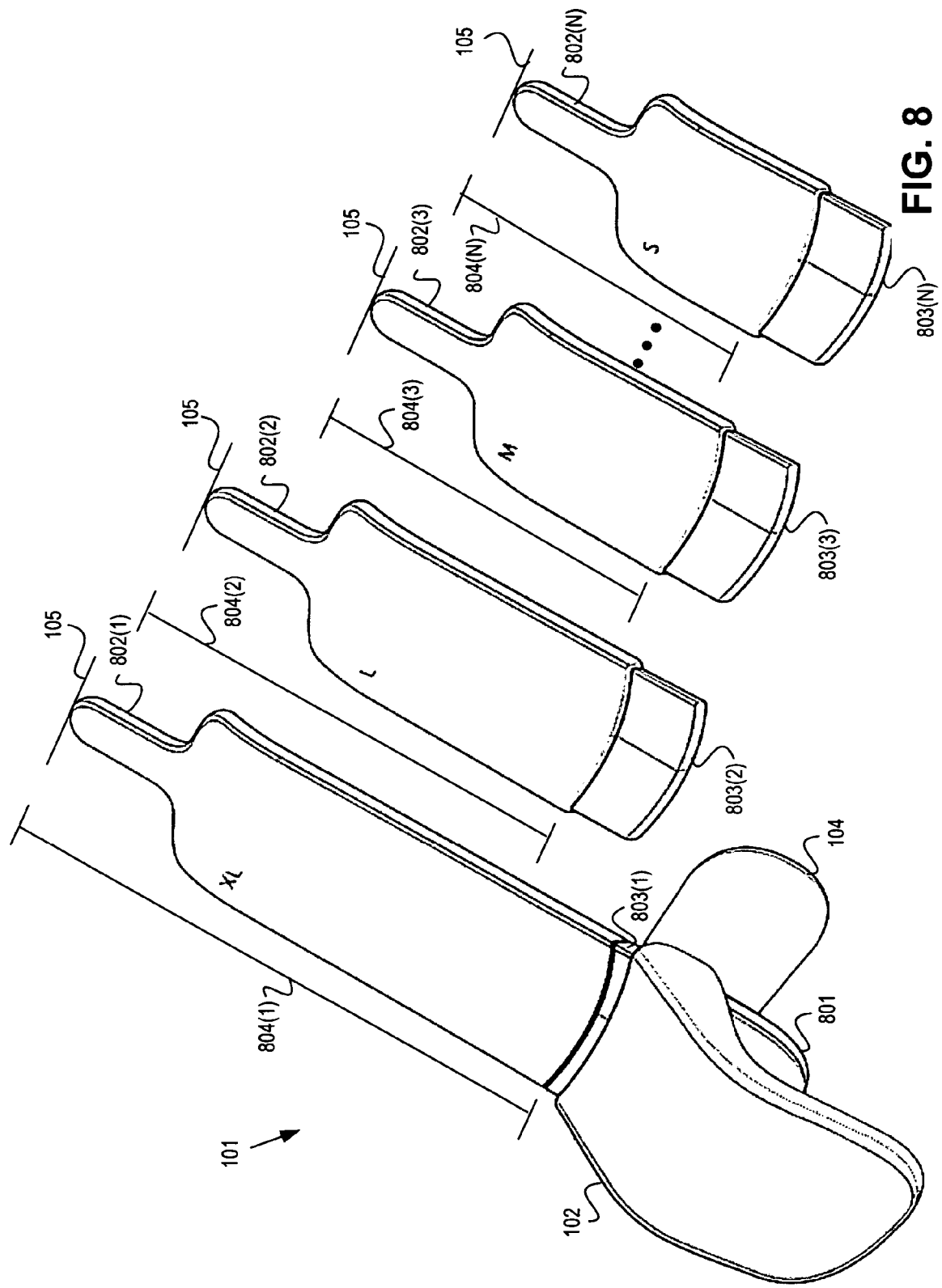
FIG. 8 illustrates one embodiment of a treatment couch including a base portion and plurality of detachable portions.

FIG. 8 illustrates one embodiment of a treatment couch including a base portion and a plurality of detachable portions. Treatment couch 101 of FIG. 8 includes a base portion 801, and a plurality of detachable portions 802(1)-(N) (e.g., multiple back-rests) of the treatment couch 101. One detachable portion 802(1) of the plurality of detachable portions 802(1)-(N) is coupled to the base portion 801 of the treatment couch 101. Each detachable back-rest 802 has a height 804. The plurality of detachable portions 802 (e.g., multiple back-rests) may be used to adjust a height of the treatment couch 101 to accommodate differing heights of patients. In one embodiment, the plurality of detachable portions 802 are used to position a head of a patient with respect to a head-end 105 of the treatment couch 101. In another embodiment, the plurality of detachable portions 802 are used to adjust an upper-half of a patient relative to a head-end 105 of the treatment couch 101.

In one embodiment, the treatment couch 101 of FIG. 8 may include a leg rest 102. Leg rest 102 may be detachable, and may have one or more pivot points for one or more articulations, as described with respect to FIGS. 7A-7D. Leg rest 102 may be coupled to extension mounting area 104. Alternatively, the treatment couch 101 of FIG. 8 may not include the leg rest 102 and/or the extension mounting area.

In one embodiment, the base portion 801 of the treatment couch 101 may be coupled to a robotic arm. Alternatively, the base portion 801 may be coupled to a stand, or to other motorized mechanisms known by those of ordinary skill in the art.

The multiple back-rests (e.g., the plurality of detachable portions 802) of treatment couch 101 may be mounted to the base portion 801. In one embodiment, the multiple back-rests 802 may include a tab portion 803 that is inserted into the base portion 801. The tab portion 803 may be used to easily remove the back-rests 802 from the base portion 801, to change the height 804 of the treatment couch 101.

The multiple back-rests may minimize the range of adjustment necessary for any given patient. One of the multiple back-rests may be a large-sized back-rest to accommodate the ninety-nine percentile male (e.g., 75.6 inches), and another a small-sized back-rest to accommodate the one percentile female (e.g., 58.1 inches). Additional back-rests between the large-sized and the small-sized back-rests may also be provided to accommodate differing heights of patients ranging between the 99 ninety-nine percentile male (e.g., 75.6) and one percentile female (e.g., 58.1 inches). The more differing-heights back-rests that are available, the lower the distance necessary for adjustment of the patient's head relative to the head-end of the treatment couch. The multiple back-rests may be stored on a rack on the wall of a treatment room. Alternatively, the multiple back-rests may be stored in other places inside or outside of the treatment room.

Figure 9A:
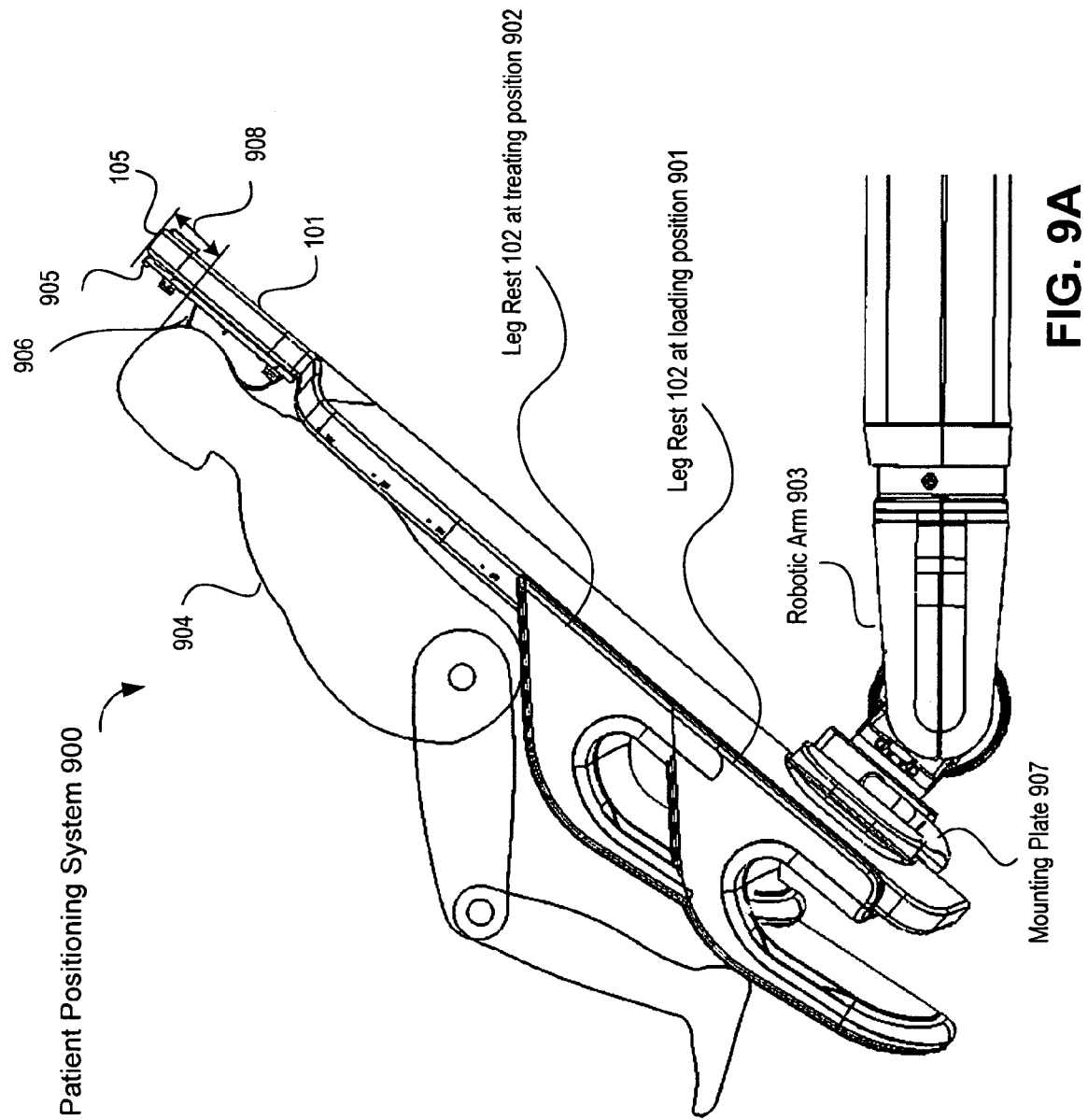
FIG. 9A illustrates one embodiment a patient positioning system, including a treatment couch, a motorized leg rest, and a robotic arm, and a patient at two positions on the treatment couch while the treatment couch is in a non-horizontal loading position.

FIG. 9A illustrates one embodiment a patient positioning system, including a treatment couch, a motorized leg rest, and a robotic arm, and a patient at two positions on the treatment couch while the treatment couch is in a non-horizontal loading position. Patient positioning system 900 includes treatment couch 101, motorized leg rest 102, and robotic arm 903. Robotic arm 903 couples to the leg rest via mounting plate 907 to a mounting area on the treatment couch 101. Alternatively, treatment couch 101 may include an extension mounting area (e.g., 104) to which the robotic arm 903 is mounted. Robotic arm 903 may include multiple degrees of freedom. In one exemplary embodiment, the robotic arm may include 6 degrees of freedom. In another exemplary embodiment, the robotic arm 903 may include components manufactured by KUKA Roboter GmbH of Germany. Alternatively, the robotic arm 903 may have less than 6 degrees of freedom, and may utilize other motorized mechanisms known by those of ordinary skill in the art used to position a treatment couch.

Treatment couch 101 of FIG. 9A may include a cushion 906 for the head of the patient 904. Cushion 906 may be secured to the treatment couch via mounting device 905. The cushion 906 provides support to the patient's head and may slide in a translational direction relative to the head-end 105 of the treatment couch 101. The cushion 906 may also be integrated into the body of treatment couch 101. In another embodiment, the mounting device 905 may be used to secure a mask for the patient 904. The mask may be used to secure the patient to the treatment couch 101 to limit the mobility of the patient 904 during treatment.

Leg rest 102 of FIG. 9A may include a motorized drive mechanism to move the leg rest 102 in a translational direction relative to the head-end 105 of the treatment couch 101. In one embodiment, the motorized drive mechanism is a rack and pinion gear. In another embodiment, the motorized drive mechanism may be a single or dual ball screw drive system. Alternatively, the motorized drive mechanism may be other drive mechanisms as described herein, and other motorized drive mechanisms known by those of ordinary skill in the art. The leg rest 102 may be detachable. The leg rest 102 may also include one or more pivot points to facilitate one or more tilting motions about one or more tilting axes. The pivot points may be used to position the leg rest to be substantially flat with respect to a plane of a top surface of the treatment couch 101.

In one embodiment, the patient 904 may be loaded onto the treatment couch 101 in a first position, such as when the treatment couch 101 is positioned in a non-horizontal position and the leg rest 102 is at a loading position 901. After loading the patient onto the treatment couch 101, the drive mechanism may move the leg rest 102 from loading position 901 to a treating position 902. Treating position 902 may be where the head of the patient 904 is positioned towards the head-end 105 of the treatment couch 101. In one exemplary embodiment, the distance (e.g., 908) between the head of the patient and the head-end 105 may have a range of approximately zero to six inches. After treatment is completed, the drive mechanism may move the leg rest 102 from the treating position 902 to the loading position 901 for unloading the patient 904 from the treatment couch 101.

Figure 9B:
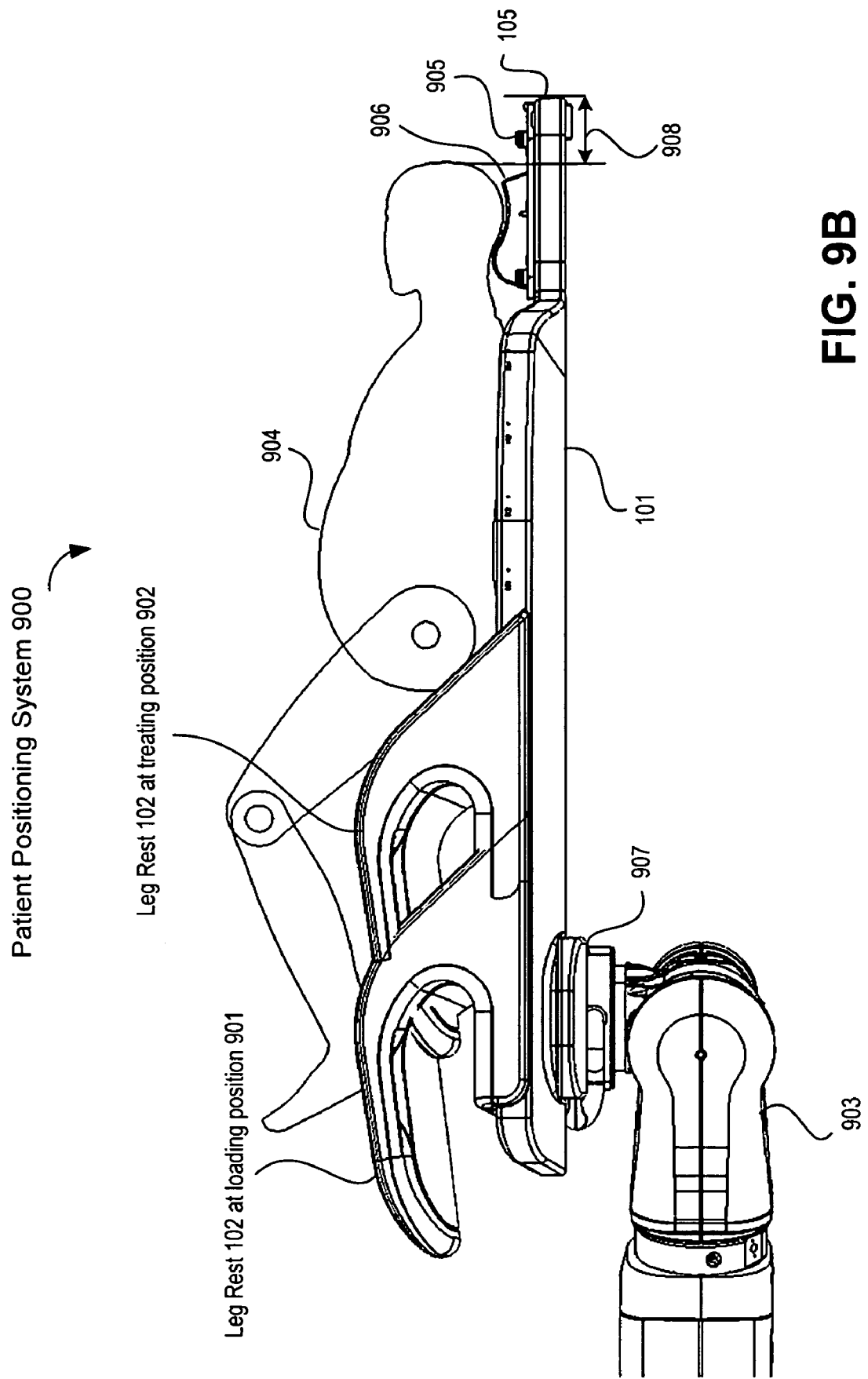
FIG. 9B illustrates the embodiment of FIG. 9A while the treatment couch is in a horizontal treatment position.

FIG. 9B illustrates the embodiment of FIG. 9A while the treatment couch is in a horizontal treatment position. In this embodiment, the patient 904 may be loaded onto the treatment couch in a first position, such as when the treatment couch 101 is positioned in a horizontal position and the leg rest 102 is at a loading position 901. After loading the patient onto the treatment couch 101, the drive mechanism may move the leg rest 102 from loading position 901 to a treating position 902. Treating position 902 may be in a position where the head of the patient 904 is positioned towards the head-end 105 of the treatment couch 101, for example, within six inches of the head-end 105 of the treatment couch. After treatment is completed, the drive mechanism may move the leg rest 102 from the treating position 902 to the loading position 901 for unloading the patient 904 from the treatment couch 101.

In one embodiment, the leg rest 102 may be moved to adjust the patient 904 to a treating position 902 from a loading position 901. Treating position 902 may be where the head of the patient 904 is positioned or aligned so that there is substantially no distance (distance 908) between the head of the patient and the head-end 105 of the treatment couch 101. In one exemplary embodiment, the distance 908 between the head of the patient 904 and the head-end 105 for the treating position 108 may have a range of approximately zero to six inches. This may allow a radiation source (not illustrated in FIG. 9A or 9B to be positioned with respect to the head of the patient with minimal interference from the treatment couch 101, or without any interference from the treatment couch 101. For example, if a shorter patient (e.g., 1 percentile female height of 58.1 inches) is loaded onto the treatment couch 101 in position 107, the patient's head will not be aligned or positioned at the top (e.g., head-end 105) of the treatment couch 101 because of the height of the shorter patient. However, by moving the leg rest 102 of the treatment couch 101 towards the head-end 105 of the treatment couch 101 (e.g., from position 107 to position 108), the patient's head may become aligned or positioned at the top (e.g., relative to the head-end 105) of the treatment couch 101.

In one embodiment, the treatment couch 101, including a motorized leg rest, is coupled to a robotic arm 903. The robotic arm 903 includes a controller. The controller positions the treatment couch 101 in one or more degrees of freedom, for example, in at least 5 degrees of freedom. In this embodiment, the motorized leg rest (e.g., leg rest 102 and corresponding drive mechanism) may be controlled independent of the motions controlled by the controller of the robotic arm 903. Alternatively, the controller of the robotic arm 903 may be used to control both the motions of the robotic arm 903 for positioning the treatment couch 101 in a treatment room, and the motions of the leg rest 102 for positioning the patient 904 on the treatment couch 101 (e.g., positioning an upper-half of a patient 904 relative to a head-end 105 of the treatment couch 101).

Figure 10A:
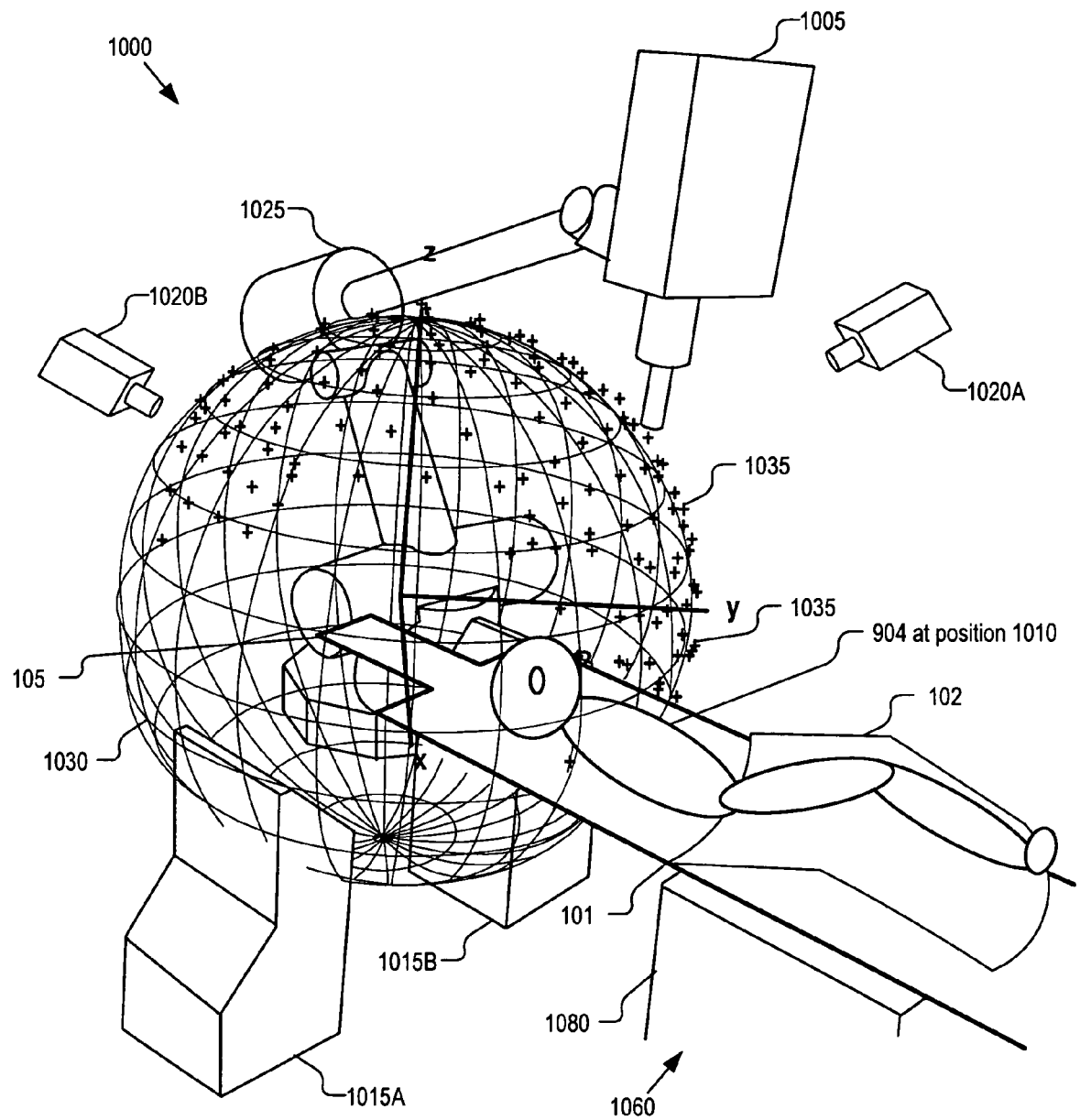
FIG. 10A is a perspective drawing illustrating a patient in a first position of a workspace of a radiation treatment system including a set of spatial nodes at which to position the radiation source, in accordance with an exemplary embodiment of the invention.

FIG. 10A is a perspective drawing illustrating a patient in a first position of a workspace of a radiation treatment system including a set of spatial nodes at which to position the radiation source, in accordance with an exemplary embodiment of the invention. The illustrated embodiment of radiation treatment system 1000 includes a radiation source 1005, detectors 1015A and 1015B (collectively 1015, also referred to as imagers), imaging sources 1020A and 1020B (collectively 1020), and a robotic arm 1025.

The illustrated embodiment also includes a patient positioning system 1060. Patient positioning system 1060 includes a treatment couch 101 and a stand 1080. Alternatively, treatment couch 101 may be coupled to a robotic arm (e.g., 903), or other motorized positioning system known by those of ordinary skill in the art. Patient positioning system 1060 includes leg rest 102. Leg rest 102 may be used to adjust an upper-half of the patient 904 relative to a head-end of the treatment couch 101. Leg rest 102 may include a motorized mechanism for adjusting the patient on the treatment couch 101. Leg rest 102 may also include one or more pivot points as described herein. In this exemplary embodiment, the patient 904 is positioned at position 1010. Position 1010 may be a loading position. The loading position may include the treatment couch 101 being in a horizontal position, or alternatively, in a non-horizontal position.

Figure 10B:
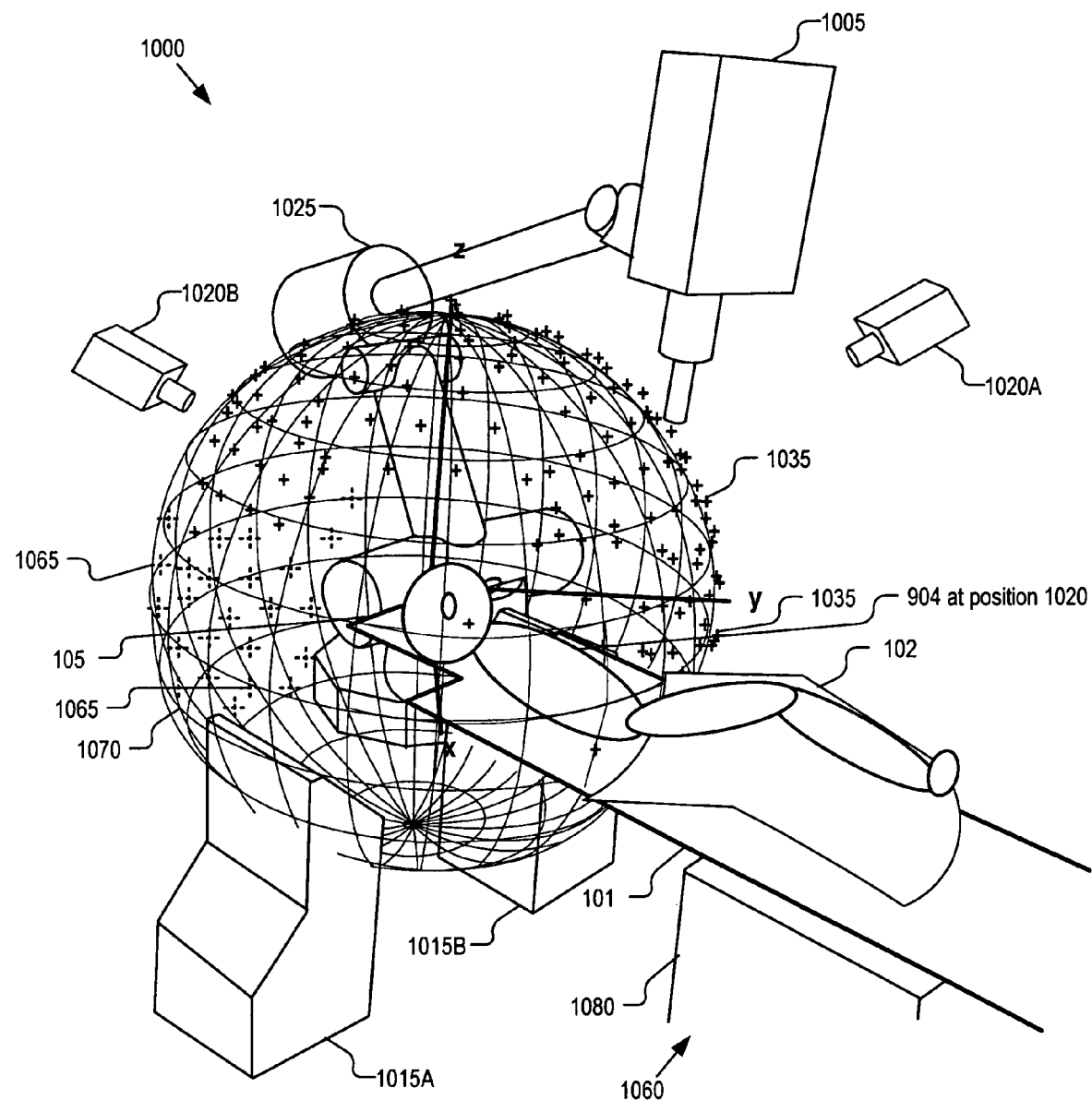
FIG. 10B is a perspective drawing illustrating the patient in a second position of the workspace of the radiation treatment system, in accordance with the embodiment of FIG. 10B.

Radiation treatment system 1000 may be used to perform radiation treatment (e.g., radiosurgery and/or radiotherapy) to treat or destroy a lesion (e.g., tumorous tissue) within a patient. During radiation treatment, the patient rests on treatment couch 101, which is maneuvered to position a volume of interest ("VOI") containing a target to a preset position or within an operating range accessible to radiation source 1005 (e.g., field of view). In one embodiment, radiation treatment system 1000 is an image guided radiation treatment system. In one exemplary embodiment, the radiation treatment system 1000 may be a frameless, image-guided robot-based therapeutic radiation treatment system utilizing a linear accelerator ("linac"), such as the CyberKnife® system developed by Accuracy, Inc. of California. Alternatively, the therapeutic radiation treatment system 1000 may be a gantry-based (iso-centric) treatment system or other type of medical operation systems. Together, imaging sources 1020 and detectors 1015 are an imaging guidance system that provides visual control over the position of treatment couch 101 and the patient thereon and the alignment of radiation source 1005 with respect to the VOI within the patient. In one embodiment, the patient positioning system treatment couch 101 may be coupled to a positioning system 1080 (not illustrated), such as robotic arm 903, that receives feedback from the imaging guidance system to provide accurate control over both the displacement and orientation of the VOI within the patient relative to radiation source 1005. In another embodiment, positioning system 1080 may be a stand, as illustrated in FIGS. 10A and 10B, or a motorized positioning system known by those of ordinary skill in the art.

In one embodiment, robotic arm 1025 has multiple (e.g., six) degrees of freedom capable of positioning the radiation source 1005 with almost an infinite number of positions and orientations within its operating envelope.

A collection of spatial nodes and associated safe paths interconnecting these spatial nodes is called a "workspace" or "node set". FIG. 10A illustrates a workspace 1030, including a number of spatial nodes 1035 each represented by a "+" symbol (only a couple are labeled). Multiple different workspaces may be created and defined for different patient work areas. For example, workspace 1030 may be spherical (as illustrated) and defined for treating VOIs residing within the head of a patient 904. Alternatively, workspace 1030 may have other geometries (e.g., elliptical) and defined for treating VOIs residing within other areas of a patient. Additionally, multiple workspaces 1030 may be defined for different portions of a patient, each having different radius or source to axis distances ("SAD"), such as 650 mm and 800 mm. The SAD is the distance between the collimator lens in radiation source 1005 and the target within the VOI. The SAD defines the surface area of the workspace. In one embodiment of an elliptical workspace, the SAD may range from 900 mm to 1000 mm. Other SADs may be used.

Spatial nodes 1035 reside on the surface of workspace 1030. Spatial nodes 1035 represent positions where the radiation source 1005 is pre-programmed to stop and delivery a dose of radiation to the VOI within the patient. During delivery of a treatment plan, robotic arm 1025 moves radiation source 1005 to each and every spatial node 1035, where a dose is determined to be delivered, following a predefined path. The predefine path may also includes some spatial nodes 1035 where no dose needs to be delivered, in order to simplify the motions of the robotic arm.

FIG. 10A illustrates a node set including an exemplary number of spatial nodes 1035 (e.g., 100 to 115). The node set may include spatial nodes 1035 substantially uniformly distributed over the geometric surface of workspace 1030. The node set includes all programmed spatial nodes 1035 and provides a workable number of spatial nodes 1035 for effectively computing treatment plan solutions for most ailments and associated VOIs. The node set provides a reasonably large number of spatial nodes 1035 such that homogeneity and conformality thresholds can be achieved for a large variety of different VOIs, while providing enough vantage points to avoid critical structures within patients. It should be appreciated that the node set may include more or less spatial nodes 1035 than is illustrated or discussed. For example, as processing power increases and experience gained creating treatment plans, the average number of spatial nodes 1035 may increase with time to provide greater flexibility and higher quality treatment plans.

FIG. 10A illustrates a patient 904 in a first position (e.g., 1010) of workspace 1030 of the radiation treatment system 1000 including a set of spatial nodes 1035 at which to position the radiation source 1005. In this exemplary embodiment, the height of patient 904 is smaller than the height of the treatment couch 101 from the head-end of the treatment couch 101 to the position of the leg rest 102. Because of the placement of the head of patient 904 the radiation source 1005 may be positioned at the exemplary spatial nodes 1035.

FIG. 10B is a perspective drawing illustrating the patient in a second position of the workspace of the radiation treatment system, in accordance with the embodiment of FIG. 10B. As previously described with respect to FIG. 10A, the height of patient 904 is smaller than the height of the treatment couch 101 from the head-end of the treatment couch 101 to the position of the leg rest 102 when the patient is in the first position 1010. However, by moving the leg rest 102 by using a motorized mechanism, as described herein in the present embodiments, relative to the head-end 105 of the treatment couch 101, the head of patient 904 may be positioned at a second position 1020. Because the head of the patient 904 is positioned closer to the head-end 105 of the treatment couch 101 in second position 1020, the available spatial nodes increases (e.g., increased spatial nodes 1065), as illustrated as dashed "+" in FIG. 10B. When the patient is positioned or aligned to the head-end 105 of the treatment couch 101 (e.g., position 1020), the available number of spatial nodes 1035 of workspace 1070 of FIG. 10B, which includes spatial nodes 1035 and increased spatial nodes 1065, is greater than the number of available number of spatial nodes of workspace 1030 when the patient is positioned at the first position 1010. In other words, by adjusting the patient (e.g., upper-half of the patient) relative to the head-end 105 of the treatment couch 101, the available workspace 1070 (e.g., including the increased number of spatial nodes 1065) of the radiation source 1005 of radiation treatment system 1000 is increased. By moving the patient from the first position 1010 to the second position 1020, the radiation source 1005 may access certain zones (e.g., spatial nodes) near the treatment couch 101 that were previously blocked by the treatment couch 101 when the patient was in the first position 1010. Having greater accessibility to those certain zones, which were previously blocked by the treatment couch 101, increases the workspace 1070 (e.g., spatial nodes at which the radiation source 1005 may deliver radiation to the target).

Figure 11A:
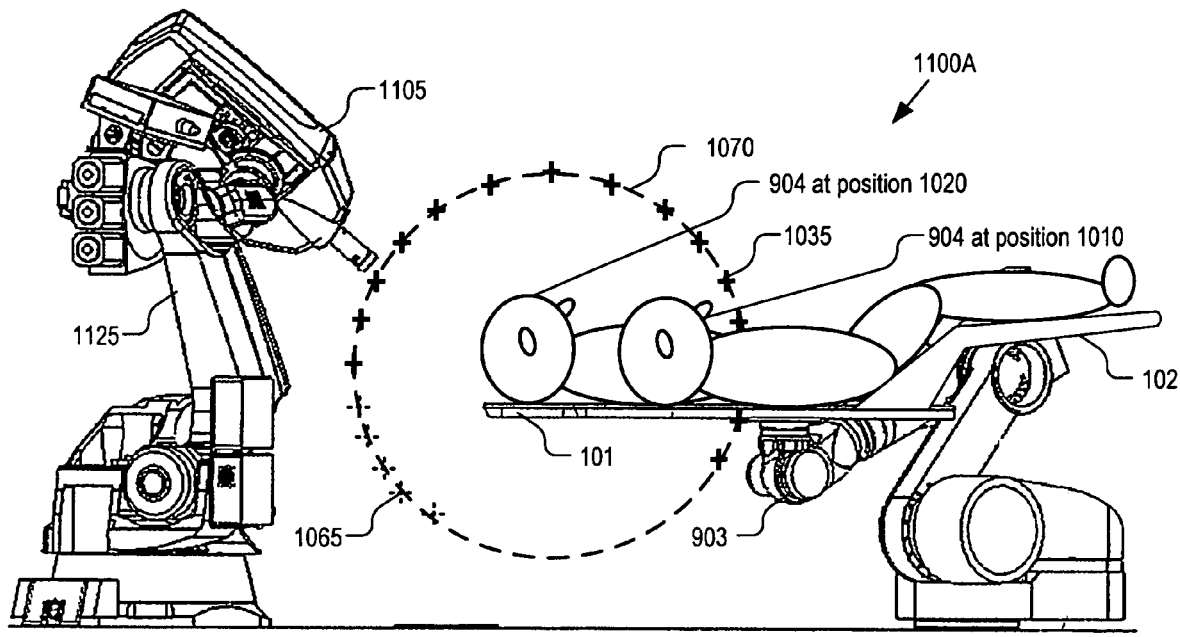
FIG. 11A is an elevational side view illustrating a cross-section of a workspace of a radiation treatment system including a node set and an increased node set, in accordance with an embodiment of the invention.
Figure 11B:
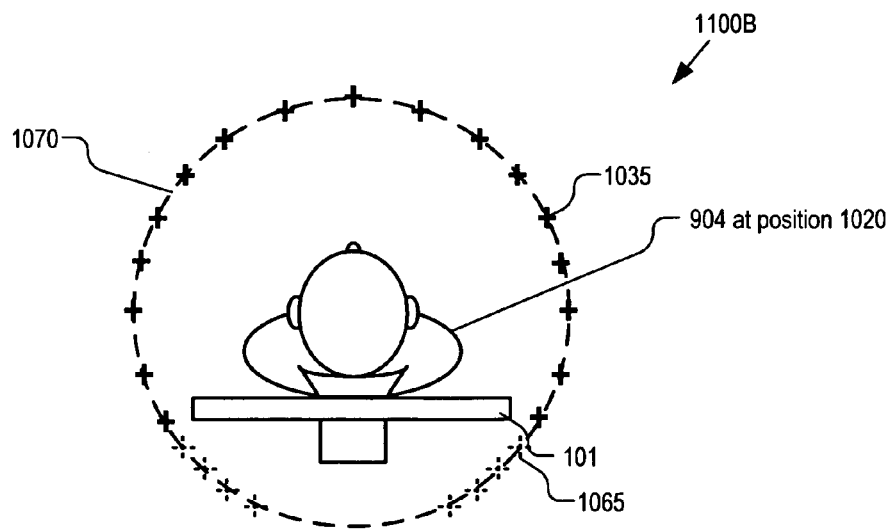
FIG. 11B is an elevational end view illustrating a cross-section of a workspace of a radiation treatment system including a node set and an increased node set, in accordance with an embodiment of the invention.

FIG. 11A and FIG. 11B are elevational side and elevational end views illustrating a cross-section of a workspace of a radiation treatment system including a node set and an increased node set, in accordance with an embodiment of the invention. Cross-sections 1100A and 1100B illustrate how a node set of workspace 1070 may have spatial nodes 1035 and increased spatial nodes 1065 evenly distributed around its surface. Other distributions are possible.

Using large or complete node sets of spatial nodes 1035 and increased spatial nodes 1065 may increase flexibility to achieve conformality and homogeneity, while minimizing risk of complications to a patient for a wide variety of different VOIs. A larger node set provides a greater number of vantage points from which to delivery a radiation beam from radiation source 1005. The greater the number of vantage points the greater the flexibility to design a treatment plan that avoids beam trajectories passing close to or through critical structures of a patient. Avoiding proximity to critical structures reduces the risks of complication to a patient.

In one embodiment, the node set of workspace 1030 (as illustrated in FIG. 10A) may be increased to be an increased node set of workspace 1070 (as illustrated and described with respect to FIG. 10B). By moving or adjusting the upper-half of patient 904 from a first position 1010 to a second position 1020, the number of node sets 1035 may increase (e.g., by increased spatial nodes 1065). Because the head of the patient 904 is positioned closer to the head-end 105 of the treatment couch 101 in second position 1020 than in the first position 1010, the available spatial nodes increases (e.g., increased spatial nodes 1065), as illustrated as dashed "+" in FIGS. 11A and 11B. For example, workspace 1070 includes spatial nodes 1035 and increased spatial nodes 1065 when the patient 904 is positioned at the second position 1020, while the workspace 1030 includes only node set 1035 when the patient 904 is positioned at the first position 1010.

In one exemplary embodiment, the leg rest may be used when acquiring a pre-treatment image (e.g., a magnetic resonance (MR) image, a computerized tomography (CT) image, fluoroscopy image, and a positron emission tomography (PET) image) of a patient in a pre-treatment position (including the treating position) for treatment planning purposes. The pre-treatment position may be recorded electronically or mechanically at the time of acquiring the pre-treatment image, and manually or automatically loaded to restore the same leg rest position during treatment. This may be done not only to ensure positioning with respect to the pre-treatment position, but also, to ensure consistent treating positions across multiple fractions (e.g., multiple treatments of the patient).

Restoration of the pre-treatment position may be used to aid in registration of the patient. Registration of a patient using a radiation system may be used in an initial patient setup as a positioning procedure for aligning a patient to be in a same position as when the patient was imaged during treatment planning. During treatment planning, pre-treatment images (as an initial reference image) of the patient are taken and used to plan radiation to be delivered by the radiation source. Subsequent images (e.g., treatment images) are then registered with the pre-treatment image in order to determine the location or displacement of the target (e.g., tumor) with respect to the pre-treatment scan (initial reference image). The displacement of the target determined by the registration may be used to adjust the patient position such that the displacement is minimized to within an operating range of the radiation treatment system. This enables the radiation source to be controlled to deliver radiation beams as specified by the treatment plan. After the patient is positioned during the initial patient setup, then the radiation may be delivered to the target of the patient from the radiation source.

Restoration of the pre-treatment position, or intra-fraction treatment positions, may be particularly helpful with a non-image guided radiation system, which relies on precise target alignment with the radiation source, as opposed to an image-guided radiation system, which enables the radiation source manipulator to track and correct for changes in patient target position during treatment delivery.

Restoration of the pre-treatment position may also be used to aid in immobilization of the patient. Immobilization may be used to maintain a constant spatial relationship between the target and the radiation source to ensure accurate dose delivery. Immobilization may be affected by the positioning of the patient on the treatment couch. Thus, restoration of the leg rest to a same position as a pre-treatment position may help immobilize the target with respect to a skeletal structure of the body, thereby, minimizing or eliminating tumor deformation and displacement. For example, during treatment of a target with the sacrum region, when a patient is positioned on the treatment couch, the patient's skeletal structure and organs comes to rest. However, by changing the position of the legs (e.g., tilting the legs at a different angle), the target (e.g., tumor) may change by displacement or by deformation based on how the legs are positioned with respect to the skeletal structure. This may be used for both image-guided and non-image-guided radiation treatment systems.

In one embodiment, a method for positioning a patient on a treatment couch may include loading a patient onto a treatment couch, in a first operation. In a second operation, mechanically adjusting an upper-half of the patient relative to a head-end of the treatment couch. In one embodiment, adjusting the upper-half of the patient may be done before loading the patient onto the couch. Alternatively, the adjusting may be done after loading the patient onto the couch. The method may further include positioning the patient in a treatment room or with respect to a radiation source in a treatment position. It should be noted that the patient may be positioned in a treatment room or with respect to the radiation source before or after the patient has been adjusted on the treatment couch relative to the head-end. Alternatively, both operations may be performed at substantially the same time. For example, after the patient is loaded onto the couch, the patient may be positioned on the couch relative to the head-end of the treatment couch while the treatment couch is positioned in a treatment room relative to a radiation source of a radiation treatment system.

Mechanically adjusting the upper-half of the patient may include moving the upper-half of the patient using a motorized drive mechanism. The motorized drive mechanism may be a rack and pinion gear. Alternatively, the motorized drive mechanism may be a single ball screw drive, such as a telescopic ball screw drive, or a dual ball screw drive. The motorized drive mechanisms may be mounted on a centerline of the treatment couch or in an off-center line, having an offset from the centerline of the treatment couch. Alternatively, other motorized drive mechanisms may be used to adjust the upper-half of the patient.

In another embodiment, mechanically adjusting the upper-half of the patient may include moving the upper-half of the patient using a manual drive mechanism. The manual drive mechanism may be a hand crank or other mechanical device known by those of ordinary skill in the art.

In another embodiment, the method may further include providing a leg rest, which has a single pivot point, to be coupled to the treatment couch, in a third operation. In a fourth operation, the method may include rotating or tilting the leg rest about a pivot axis of the pivot point. Alternatively, the method may include providing a leg rest, which has multiple pivot points, to be coupled to the treatment couch, in a third operation; and in a fourth operation, rotating or tilting the leg rest about the multiple pivot axes of the multiple pivot points. In one exemplary embodiment, the multiple pivot points may be used to position the leg rest to be substantially flat with respect to a plane of a top surface of the treatment couch. Having the leg rest be substantially flat with respect to the treatment couch may allow the leg rest from being removed for prone treatments. In one embodiment, the method may include positioning the leg rest to be substantially flat with respect to a plane of a top surface of the treatment couch, in a third operation.

The method may further include detaching the leg rest from the treatment couch, in a fifth operation. In some embodiments, the leg rest may be removed for prone treatments or so that it is not in the way of the radiation source or other objects used in the treatment.

In another embodiment, the treatment couch may include a base portion and a plurality of detachable portions, of which one, is coupled to the base portion at a time. The method, implementing this design, may further include detaching a first detachable portion from a base portion of a treatment couch, in a third operation. The method may also include attaching a second detachable portion to the base portion to adjust a height of the treatment couch to accommodate differing heights of patients, in a fourth operation.

In another embodiment, the treatment couch may include a base portion and a back-rest portion coupled to the base portion, and the method may further include adjusting the upper-half of the patient comprises adjusting a height of the back-rest portion of the treatment couch to accommodate differing heights of patients, in a third operation.

The embodiments described herein may also be implemented in a treatment couch of a patient positioning system, used in connection with a radiation treatment system. In one embodiment, the radiation treatment system may be a robot-based linear accelerator treatment system. Alternatively, the radiation treatment system may be a gantry-based radiation treatment system.

The patient positioning system may include a treatment couch coupled to a stand, or alternatively, to a positioning system. In one embodiment, the positioning system may be a robotic arm, having one or more degrees of freedom. Alternatively, the positioning system may be other motorized mechanisms known by those of ordinary skill in the art used to position a treatment couch.

In one embodiment, a method, implementing the patient positioning and radiation treatment systems, may include providing a treatment couch coupled to a first robotic arm, in a first operation, moving the treatment couch along one or more rotational degrees of freedom, in a second operation, and moving an upper-half of a patient relative to a head-end of the treatment couch, in a third operation. The method may further include providing a linear accelerator coupled to a second robotic arm, the second robotic arm to move the linear accelerator with respect to a treatment target of the patient, in a fourth operation. The method may further include providing an imaging system having an imaging field of view, and maintaining the treatment couch substantially outside of the imaging field of view for all supported treatment positions by moving the upper-half of the patient relative to the head-end of the treatment couch.

In another embodiment, the method may further include providing a leg rest having a pivot point to be coupled to the treatment couch, in a third operation, and rotating or tilting the leg rest about the pivot point, in a fourth operation. Alternatively, the third and fourth operations may include providing a leg rest having a having a plurality of pivot points to be coupled to the treatment couch, and rotating or tilting the leg rest about the plurality of pivot points. In one exemplary embodiment, the multiple pivot points may be used to position the leg rest to be substantially flat with respect to a plane of a top surface of the treatment couch. Having the leg rest be substantially flat with respect to the treatment couch may allow the leg rest from being removed for prone treatments. In one embodiment, the method may include positioning the leg rest to be substantially flat with respect to a plane of a top surface of the treatment couch, in a third operation. The method may further include detaching the leg rest from the treatment couch in a fifth operation.

In another embodiment, the treatment couch may include a base portion and a plurality of detachable portions, of which one is coupled to the base portion at a time. The method, implementing this design, may further include detaching a first detachable portion from a base portion of a treatment couch, in a third operation. The method may also include attaching a second detachable portion to the base portion to adjust a height of the treatment couch to accommodate differing heights of patients, in a fourth operation.

In another embodiment, the treatment couch may include a base portion and a back-rest portion coupled to the base portion, and the method may further include adjusting the upper-half of the patient comprises adjusting a height of the back-rest portion of the treatment couch to accommodate differing heights of patients, in a third operation. herein adjusting the upper-half of the patient comprises adjusting the upper-half of the patient before/after or during loading the patient onto the treatment couch It should be noted that the embodiments described herein are not limited to radiation treatment systems. The embodiments described herein may also be used in connection with other medical treatment, such as a positioning couch for an operating room, a positioning couch for a diagnostic x-ray machine, a positioning chair for dental procedures, treatment chairs, and other medical patient support or positioning couches.

As previously discussed, the embodiments described herein are not limited to a treatment couch used for medical treatment. The embodiments described herein may also be used in connection with other non-medical treatment systems, such as a couch (which may otherwise be referred to as a chair, or otherwise, in particular fields of application) for a simulator, video or arcade game system. The embodiments described herein may also be used as a loading mechanism for an amusement park ride, for military machinery, or for heavy machinery to position, reposition, align, or adjust a body (e.g., human or animal body) into a confined space (e.g., into a gunner position of a tank) in a translational direction. Alternatively, the embodiments described herein may be used in other types of applications that involve positioning a body with respect to one end of a couch in a translational direction.

Embodiments of the present invention include various operations, which will be described below. These operations may be performed by hardware components, software, firmware, or a combination thereof. As used herein, the term "coupled to" may mean coupled directly or indirectly through one or more intervening components. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Certain embodiments may be implemented as a computer program product that may include instructions stored on a machine-readable medium. These instructions may be used to program a general-purpose or special-purpose processor to perform the described operations. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; electrical, optical, acoustical, or other form of propagated signal (e.g., carrier waves, infrared signals, digital signals, etc.); or another type of medium suitable for storing electronic instructions.

Additionally, some embodiments may be practiced in distributed computing environments where the machine-readable medium is stored on and/or executed by more than one computer system. In addition, the information transferred between computer systems may either be pulled or pushed across the communication medium connecting the computer systems.

A "target" as discussed herein may be an anatomical feature(s) of a patient such as a pathological anatomy (e.g., tumor, lesion, vascular malformation, nerve disorder, etc.) or normal anatomy and may include one or more non-anatomical reference structures.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the application of a beam(s) and "target" may refer to a non-anatomical object or area.

The controller(s) described herein may include one or more general-purpose processing devices such as a microprocessor or central processing unit, or the like. Alternatively, the controller may include one or more special-purpose processing devices such as a digital signal processor (DSP), an application specific integrated circuit (ASIC), a field programmable gate array (FPGA), or the like. In an alternative embodiment, for example, the controller may be a network processor having multiple processors including a core unit and multiple microengines. Additionally, the controller may include any combination of general-purpose processing device(s) and special-purpose processing device(s).

Although the operations of the method(s) herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. An apparatus, comprising:
   a couch
   a leg rest coupled to the couch; and
   a drive mechanism coupled to the leg rest, the drive mechanism to move the leg rest in a translational direction to adjust an upper-half of a body with respect to a head-end of the couch, wherein the drive mechanism is a motorized drive mechanism, and wherein the motorized drive mechanism comprises a rack and pinion gear, comprising:
      a motor coupled to the couch;
      a pinion;
      a drive shaft coupled to the motor and the pinion; and
      a rack having a plurality of teeth coupled to the leg rest, the motor to drive the pinion along the plurality of teeth, the motor to move the leg rest in a translational direction relative to a head-end of the couch.

2. The apparatus of claim 1, wherein the motorized drive mechanism is positioned at a centerline of the couch.

3. The apparatus of claim 1, wherein the motorized drive mechanism is positioned at an off-center line, the off-center line having an offset distance from a centerline of the couch.

4. An apparatus, comprising:
   a couch
   a leg rest coupled to the couch; and
   a drive mechanism coupled to the leg rest, the drive mechanism to move the leg rest in a translational direction to adjust an upper-half of a body with respect to a head-end of the couch, wherein the drive mechanism is a motorized drive mechanism, and wherein the motorized drive mechanism comprises a single ball screw drive system coupled to the leg rest and the couch, the single ball screw drive system to move the leg rest in a translational direction relative to a head-end of the couch, wherein the single ball screw system comprises:
      a motor;
      a ball screw coupled to the motor; and
      a car operatively coupled to the ball screw and the leg rest, the motor to move the leg rest in a translational direction relative to a head-end of the couch.

5. The apparatus of claim 4, wherein the single ball screw is a telescopic ball screw.

6. The apparatus of claim 4, wherein the motorized drive mechanism is positioned at a centerline of the couch.

7. The apparatus of claim 4, wherein the motorized drive mechanism is positioned at an off-center line, the off-center line having an offset distance from a centerline of the couch.

8. An apparatus, comprising:
a couch
a leg rest coupled to the couch; and
a drive mechanism coupled to the leg rest, the drive mechanism to move the leg rest in a translational direction to adjust an upper-half of a body with respect to a head-end of the couch, wherein the drive mechanism is a motorized drive mechanism, and wherein the motorized drive mechanism comprises a dual ball screw drive system coupled to the leg rest, the dual ball screw drive system to move the leg rest in a translational direction relative to a head-end of the couch, wherein the dual ball screw drive system comprises:
a motor coupled to the couch;
a first ball screw coupled to the motor;
a first car operatively coupled to the first ball screw and the leg rest;
a second ball screw coupled to the motor; and
a second car operatively coupled to the second ball screw and the leg rest, the motor to move the leg rest in a translational direction relative to a head-end of the couch.

9. A system, comprising:
a radiation treatment system comprising a radiation source; and
a patient positioning system to position a patient with respect to the radiation source of the radiation treatment system, the patient positioning system comprising:
a treatment couch;
a leg rest coupled to the treatment couch; and
a drive mechanism coupled to the leg rest, the drive mechanism to move the entire leg rest in a translational direction to adjust an upper-half of a body of a patient with respect to a head-end of the treatment couch.

10. The system of claim 9, wherein the patient positioning system comprises a controller, the controller to move the treatment couch along one or more degrees of freedom, and to adjust the upper-half of the body relative to the head-end of the treatment couch as an additional degree of freedom.

11. The system of claim 9, wherein the radiation treatment system is at least one of a gantry-based radiation treatment system or a robot-based linear accelerator system.

12. The system of claim 9, wherein the patient positioning system is a robot-based patient positioning system, the robot-based patient positioning system comprising:
the treatment couch; and
a robotic arm coupled to the treatment couch, the robotic arm to move the treatment couch along one or more degrees of freedom.

13. The system of claim 12, wherein the robotic arm positions the treatment couch in at least three degrees of freedom.

14. The system of claim 12, wherein the robotic arm positions the treatment couch in five degrees of freedom.

15. The system of claim 9, further comprising means for increasing an available workspace of a radiation source of a radiation treatment system.

16. The system of claim 9, further comprising means for positioning a head of the patient to a treating position on the treatment couch regardless of a height of the patient.

17. The system of claim 9, wherein the leg rest of the treatment couch further comprises one pivot point, the pivot point to facilitate a tilting motion of the leg rest.

18. The system of claim 9, wherein the leg rest of the treatment couch further comprises multiple pivot points, the multiple pivot points to facilitate multiple tilting motion of the leg rest.

19. The system of claim 9, wherein the leg rest of the treatment couch further comprises multiple pivot points, the multiple pivot points to position the leg rest to be substantially flat with respect to a plane of a top surface of the treatment couch.

20. The system of claim 9, wherein the leg rest is detachable.

21. The system of claim 9, wherein the treatment couch comprises:
a base portion; and
a plurality of detachable portions of the treatment couch, wherein one detachable portion is coupled to the base portion of the treatment couch, the plurality of detachable portions to adjust a height of the treatment couch to accommodate differing heights of patients.

22. The system of claim 9, wherein the treatment couch comprises:
a base portion; and
a ratchet portion coupled to the base portion, the ratchet portion to adjust a height of the treatment couch to accommodate differing heights of patients.

23. The system of claim 9, wherein the drive mechanisms comprises at least one of a telescopic ball screw drive system, a single ball screw drive system, a dual ball screw drive system including one motor, a dual ball screw drive system including two motors, a linear actuator, a pneumatic cylinder, or a regular drive screw driven by stepper motor.

24. The system of claim 9, further comprising a sliding member coupled to the leg rest, the sliding member to move in the translational direction with the leg rest, wherein the sliding member prevents the upper-half of the body from being pinched between the leg rest and the treatment couch as the leg rest moves in the translational direction.

25. A method, comprising:
moving a treatment couch along one or more degrees of freedom using a robotic arm; and
moving an upper-half of a body of a patient relative to a head-end of the treatment couch by moving an entire leg rest coupled to the treatment couch in a translational direction using a mechanical mechanism.

26. The method of claim 25, further comprising providing a linear accelerator coupled to a second robotic arm, the second robotic arm to move the linear accelerator with respect to a treatment target of the patient.

27. The method of claim 25, further comprising:
providing an imaging system having an imaging field of view; and
maintaining the treatment couch substantially outside of the imaging field of view for all supported treatment positions by moving the upper-half of the body relative to the head-end of the treatment couch.

28. The method of claim 25, further comprising:
providing a leg rest having a pivot point to be coupled to the treatment couch; and
rotating the leg rest about the pivot point.

29. The method of claim 25, further comprising:
providing a leg rest having a plurality of pivot points to be coupled to the treatment couch; and
rotating the leg rest about the plurality of pivot points.

30. The method of claim 25, further comprising positioning the leg rest to be substantially flat with respect to a plane of a top surface of the treatment couch.

31. The method of claim 25, further comprising detaching the leg rest from the treatment couch.

32. The method of claim 25, wherein the treatment couch comprises a base portion and a plurality of detachable portions, wherein a first detachable portion is coupled to the base portion and wherein mechanically adjusting the upper-half of the body comprises:

detaching the first detachable portion from the base portion; and attaching a second detachable portion to the base portion to adjust a height of the treatment couch to accommodate differing heights of patients.

33. The method of claim 25, wherein the treatment couch comprises a base portion and a back-rest portion coupled to the base portion, and wherein mechanically adjusting the upper-half of the body comprises adjusting a height of the back-rest portion of the treatment couch to accommodate differing heights of patients.

* * * * *